US012133739B2

(12) United States Patent
Tseng et al.

(10) Patent No.: US 12,133,739 B2
(45) Date of Patent: Nov. 5, 2024

(54) USE OF BRAIN AGE MODEL IN PREDICTION OF BRAIN ATROPHY

(71) Applicants: AcroViz USA Inc., Dover, DE (US); Taipei Medical University, Taipei (TW)

(72) Inventors: Wen-Yih Tseng, Taipei (TW); Yung-Chin Hsu, New Taipei (TW); Lung Chan, New Taipei (TW); Chien-Tai Hong, New Taipei (TW); Yueh-Hsun Lu, New Taipei (TW); Jia-Hung Chen, New Taipei (TW); Li-Kai Huang, New Taipei (TW)

(73) Assignees: ACROVIZ USA INC., Dover, DE (US); TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 18/539,555

(22) Filed: Dec. 14, 2023

(65) Prior Publication Data
US 2024/0206801 A1  Jun. 27, 2024

Related U.S. Application Data

(63) Continuation of application No. 18/225,312, filed on Jul. 24, 2023, now Pat. No. 11,883,184, which is a continuation-in-part of application No. 17/992,005, filed on Nov. 22, 2022, now Pat. No. 11,751,798, which is a continuation of application No. (Continued)

(51) Int. Cl.
*A61B 5/00* (2006.01)
*A61B 5/055* (2006.01)
*G06T 7/00* (2017.01)

(52) U.S. Cl.
CPC ............ *A61B 5/4088* (2013.01); *A61B 5/055* (2013.01); *A61B 5/7275* (2013.01); *G06T 7/0012* (2013.01); *G06T 2207/10092* (2013.01); *G06T 2207/30016* (2013.01)

(58) Field of Classification Search
CPC ..... A61B 5/4088; A61B 5/055; A61B 5/7275; G06T 7/0012; G06T 2207/10092; G06T 2207/30016
See application file for complete search history.

(56) References Cited

U.S. PATENT DOCUMENTS 6,169,981 B1 * 1/2001 Werbos .............. G05B 13/0285
706/26
8,626,264 B1 * 1/2014 Beran ................... G16H 50/20
600/407

(Continued)

OTHER PUBLICATIONS

Sabuncu, Mert R "Clinical Prediction from Structural MRI: A Large-Scale Empirical Study" Neuroinformatics. (Year: 2014).*

*Primary Examiner* — Molly Wilburn
(74) *Attorney, Agent, or Firm* — Locke Lord LLP; Tim Tingkang Xia, Esq.

(57) ABSTRACT

A method of predicting a brain atrophy condition for an individual using the individual's predicted age difference (PAD). The method comprises acquiring at least one brain image of the individual; processing the brain image to obtain at least one feature of the brain image; generating a PAD value of the individual based on the at least one feature of the image; and determining a brain atrophy condition of the individual based on the PAD value.

16 Claims, 25 Drawing Sheets

Related U.S. Application Data

17/704,287, filed on Mar. 25, 2022, now Pat. No. 11,589,800.

(60) Provisional application No. 63/216,028, filed on Jun. 29, 2021.

(56) References Cited

U.S. PATENT DOCUMENTS

| | | | |
|---|---|---|---|
| 10,365,340 B1* | 7/2019 | Lou | G01R 33/4806 |
| 11,263,749 B1* | 3/2022 | Purushottam | G16H 15/00 |
| 2010/0249573 A1* | 9/2010 | Marks | A61B 5/055 |
| | | | 600/411 |
| 2017/0039708 A1* | 2/2017 | Henry | A61B 5/4041 |
| 2021/0228079 A1* | 7/2021 | Betrouni | A61B 5/7246 |
| 2022/0122250 A1* | 4/2022 | Besson | G06T 7/0012 |

* cited by examiner

Algorithm: Estimate $\beta$ and $v$

1. Inputs: The pseudo $b_0$ image $f_0$ and the real $b_0$ image $\tilde{f}_1$.
2. Initialize $\beta = 0$ and $v = 0$
3. Compute $\varphi$ and $e^{\beta}$
4. Repeat until convergence Compute $g_{\beta}$ and $H_{\beta}$, then Gauss-Newton update $\beta$ Compute $g_v$ and $H_v$, then Gauss-Newton update $v$ Compute $\varphi$ and $e^{\beta}$

FIG. 19

USE OF BRAIN AGE MODEL IN PREDICTION OF BRAIN ATROPHY

CROSS-REFERENCE TO RELATED PATENT APPLICATION

This application is a continuation of U.S. patent application Ser. No. 18/225,312, filed on Jul. 24, 2023.

The U.S. patent application Ser. No. 18/225,312 is a continuation-in-part of U.S. patent application Ser. No. 17/992,005, filed on Nov. 22, 2022. The U.S. patent application Ser. No. 17/992,005 is a continuation of U.S. patent application Ser. No. 17/704,287, filed Mar. 25, 2022, which further claims priority to and the benefit of U.S. Provisional Patent Application Ser. No. 63/216,028, filed Jun. 29, 2021. All of U.S. patent application Ser. No. 18/225,312, U.S. patent application Ser. No. 17/992,005, U.S. patent application Ser. No. 17/704,287 and U.S. Provisional Patent Application Ser. No. 63/216,028 are incorporated herein in their entirety by reference.

FIELD OF THE INVENTION

The present disclosure relates to the technical field of using brain age obtained via brain image analysis in prediction of cognitive decline of patients, in particular, brain atrophy.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

In clinical practice, physicians use various cognitive tests to assess cognitive status and/or impairment due to dementia. The cognitive tests assessing cognitive status include dementia assessment tests and neuropsychological tests. Dementia assessment tests are developed based on clinically-relevant cognitive symptoms, while neuropsychological tests are developed based on the performance in different psychological domains. Dementia assessment tests that are widely used include the Clinical Dementia Rating (CDR), Mini-Mental State Examination (MMSE), Montreal Cognitive Assessment (MoCA), AD8, Alzheimer's Disease Assessment Scale-Cognitive Subscale (ADAS-cog), Alzheimer's Disease Co-operative Study ADL Scale for Mild Cognitive Impairment (ADCS-ADL-MCI), and Neuropsychiatric Inventory (NPI). A typical neuropsychological evaluation will assess a person's general intelligence, attention and concentration, learning and memory, reasoning and problem solving, language, visual-spatial skills (perception), motor and sensory skills, mood and behavior. An example of such evaluation is Repeatable Battery for the Assessment of Neuropsychological Status (RBANS).

The clinical dementia rating (CDR) is a score estimated during a semi-structure interview used for staging the severity of dementia in Alzheimer's disease (AD) (Hughes et al., 1982) or non-AD dementia (Kazui et al., 2016). Compared with neuropsychological tests, the interview for the CDR focuses on patients' daily functioning and, therefore, is more congruent with standard diagnostic criteria of dementia (Lim et al., 2007).

The CDR interview is conducted by certified physicians or nurses, and administered to patients and appropriate informants. The interview consists of 6 different domains, i.e. memory, orientation, judgment and problem solving, community affairs, home and hobbies, and personal care. The functional impairment of each domain is graded by a five-point scale system: none=0, questionable=0.5, mild=1, moderate=2, severe=3. The scores over the 6 domains are then converted to a global score of the CDR. The CDR score has been validated to be reliable to diagnose dementia and to grade the dementia severity (Morris, 1993). To date, the CDR has been included by professional societies worldwide in the guideline of dementia care and diagnosis (Petersen et al., 2018).

However, current CDR has two significant limitations. The first imitation of the CDR is its inability to predict future outcome of the CDR in the upcoming 2 to 3 years. Although the CDR is reliable to grade the dementia severity, it cannot predict the progression of dementia. CDR future outcome is clinically important because medical professionals not only assess the severity of dementia of a patient, but also want to know whether and how fast dementia will be worsened in a few years to come. This limitation is clinically relevant especially in patients with very mild or questionable dementia, i.e. CDR=0.5. The outcome of these patients is heterogeneous, some may progress to dementia (CDR=1 or higher), some may turn to normal cognition (CDR=0), and some may stay in the same CDR (Daly et al., 2000). To address this limitation, some studies demonstrated that the sum scores of the six domains, i.e. sum of boxes (SOB) (O'Bryant et al., 2008), or the subscale score in the orientation domain (Kim et al., 2017), or combination of SOB with additional memory test (Lee et al., 2006) could be useful to predict dementia progression. However, all of the above measures rely heavily on the interview, and so they are affected by clinician's judgement, informant's reliability and cultural difference (Lim et al., 2007), which is the second limitation of the CDR.

Regarding this second limitation, the CDR has stringent conditions for a successful interview. It requires well trained medical professionals and availability of reliable informants to ensure the accuracy of the CDR. Trained professionals or reliable informants may be lacking in less developed or supported areas, undermining the availability of accurate CDR.

To address these limitations, Maillard et al. addressed the two limitations altogether by using the free water (FW) content, a metric derived from post-processing of the brain diffusion MRI. They reported that higher baseline FW was significantly associated with higher baseline CDR, and higher probability to change to a higher CDR score in later interviews (Maillard et al., 2019). In addition, to address the second limitation, Beheshti et al. estimated PAD on the basis of individual's morphometric features of gray matter of the brain extracted from T1-weighted (T1w) MRI, and found that PAD was associated with the scores of several clinical assessments of dementia including the CDR (Beheshti et al., 2018).

However, all existing methods/discoveries for addressing CDR limitations has their own limitations and disadvantages. For example, Beheshti et al. demonstrated that PAD was associated with the CDR, but it fails to report how PAD could predict the future outcome of the CDR. O'Bryant et al., Kim et al. and Lee et al. used the information obtained from interview to predict CDR outcome, however, all of the scores they measure rely on interview, and so they are affected by clinician's judgement, informant's reliability and cultural difference. Maillard's FW metric has been shown to be associated with the CDR at the baseline and it can also predict the CDR change in later visits. However, FW may be confounded by cerebral atrophy in pixels neighboring the ventricles and cerebral sulci due to the partial volume effect of the cerebrospinal fluid (CSF).

Therefore, a method based on MRI scanning data of an individual patient that can predict the dementia progression of a given CDR and is free of these limitations is imperatively needed.

In another aspect of the field, diffusion MRI is widely used as a tool in understanding the morphometric features of an individual's brain. However, the diffusion-weighted images (DWI) comprised in a diffusion MRI (dMRI) data suffer from various artefacts, which impairs the medical professionals in estimating the PAD. Among them, the artefact of susceptibility-induced distortions is the most notorious since it greatly degrades the performance of dMRI analysis. This artefact is usually corrected retrospectively by measuring or estimating the "field map", which represents how a point in the undistorted space displaces (or distorts in the distortion correction context) to the distorted space. The field map is a 3D scalar field since DWI is usually assumed to distort along the phase-encoding (PE) direction due to low acquisition bandwidth.

The correction method could be roughly divided into three categories. The first is field map-based, this method explicitly measures the field map by acquiring two gradient echo images with exact scanning parameters except for the echo time (TE), then the field map is the phase differences between the two images divided by the differences of the TE values (Jezzard et al., 1998) The second is reverse gradient-based (Andersson et al., 2003; Irfanoglu et al., 2015; Hedouin et al., 2017), where two $b_0$ images (or two complete dMRI datasets) with reverse PE gradients are acquired. The $b_0$ images here refer to the DWI whose b-value=0 s/mm$^2$, i.e., without applying the diffusion-sensitive gradients. The basic idea behind this category is that the two $b_0$ images (or the two dMRI datasets) would have reverse distortions, hence the field map could be estimated by registering them to their "midpoint" image, which is theoretically the undistorted image. The last is anatomical image-based (Huang et al., 2008), in this category, the real $b_0$ image is registered to a pseudo $b_0$ image, which is constructed from the anatomical images, such as T1-weighted (T1w) image or T2-weighted (T2w) image. Since the anatomical images are free of distortions, the estimated displacement map of the registration could be considered as a surrogate of the field map. Technically, both the reverse gradient-based and the anatomical image-based methods greatly involve registration calculations, therefore, some efforts have been made to combine them by regarding the pseudo $b_0$ images as the midpoint images in the reverse gradient-based methods; this approach has been shown to improve the performance of distortion correction (Irfanoglu et al., 2015).

However, the above identified methods suffer from disadvantages that significantly limit the accuracy of the dMRI data.

In particular, the anatomical image-based methods use the anatomical image (T1w or T2w) to construct the pseudo $b_0$ image, which is used as the reference image to drive the correction. Correction methods in this category estimate the field map by non-linearly registering the real $b_0$ image (distorted) to align with the pseudo $b_0$ image (distortion-free). When the images are aligned well, the image discrepancy shall be low. Therefore, the goodness of the alignment is usually measured by similarity metrics such as sum of squared differences (SSD) (Huang et al., 2008), normalized mutual information (NMI) (Bhushan et al., 2015), correlation ratio (CR) (Bhushan et al., 2015), or cross-correlation (CC) (Irfanoglu et al., 2015).

Non-linear registration is an ill-posed problem, so it is easy to fail in nature, particularly when the images have large discrepancy. Two primary sources contribute to the image discrepancy, one is the spatial discrepancy, which is due to the susceptibility-induced distortions, and the other is the contrast discrepancy, which is the intensity biases between the real $b_0$ image and the pseudo $b_0$ image. The conventional correction methods assume that the image discrepancy is entirely caused by the susceptibility-induced distortions and disregard the contribution of the intensity biases. In this manner, the overfitting problem may become significant for regions with large intensity biases, leading to wrong point-by-point correspondence and wrong field map.

One of the solutions is to use the cost functions which are less sensitive to the contrast discrepancy, such as NMI, CR, or CC. However, estimations using these cost functions are easy to be trapped in local minima (or maxima, depends on the cost functions), rendering the spatial discrepancy originated from the susceptibility-induced distortions not corrected very well (Bhushan C et al., 2015). Another solution is to adjust the hyperparameters of the correction method to make the field map smoother, consequently lowering the sensitivity of image discrepancy. Similar to the previous approach, the lower sensitivity would lead the real distortions not corrected very well.

In addition, some of the previous studies use general-purpose 3D registration correction method, such as Large Deformation Diffeomorphic Metric Mapping (LDDMM) (Beg et al., 2005; Miller et al., 2006) and Advanced Normalization Tools (ANTs) (Avants et al., 2008), to conduct the registration. Employing the 3D registration correction method to solve the 1D distortion correction problem has at least two drawbacks. First, the calculated free-form deformations have to be further constrained to along the PE direction (Irfanoglu et al., 2015), leading to unnecessary calculations. The second, which is more serious, is that the convergence of the registration may not always correspond to the convergence of distortion correction because the registration correction method have higher degrees of freedom than the distortion problem per se.

Therefore, a method for correcting and/or reducing artefacts in dMRI data of an individual's brain is necessary for effectively calculating and predicting the dementia progression of a given CDR.

In another aspect of the invention, in addition to the prediction of CDR, treatments for cognitive impairment patients require a method for predicting their therapeutic effects.

Pharmacological or non-pharmacological treatments have been actively developed to find solutions to cure the disease or delay the progression of cognitive decline. Despite enormous resources and efforts been invested, many therapeutic agents failed to prove the efficacy of the treatment of neurodegenerative dementia in clinical trials. Currently, cholinesterase inhibitor (ChEI) and memantine, an NMDA receptor antagonist, are the only pharmacological agents approved by US Food and Drug Administration (FDA), and have been routinely used in clinical setting. ChEI increases the concentration of acetylcholine in the brain by delaying the breakdown of acetylcholine released into synaptic clefts and so enhances cholinergic neurotransmission (Birks, 2006). It is the first pharmacological agents approved by FDA in 1997, and has become the mainstay of treatment for patients with mild to moderate degrees of dementia.

Being licensed and reimbursed by National Health Systems in most countries, ChEI drugs such as donepezil, galantamine, or rivastigmine are used as the standard treatment of neurodegenerative dementia. Clinical trials have shown that patients are modestly benefitted by ChEI with improved short-term and long-term outcomes in active daily living and neurocognitive functions (Xu et al., 2021; Yang et al., 2018). However, clinical practice reveals that only 30 to 60 percent of patients show modest clinical response (Pozzi et al., 2022). In addition, adverse events of gastrointestinal symptoms may be intolerable that physicians must make decisions among drug dose tailoring, drug type switching, or treatment termination. It would be helpful to predict response prior to the treatment. Subsequent observational studies have identified various potential predictors of treatment response, although not totally consistent, they include age, sex, education level, cognitive function at baseline, white matter hyperintensity, medial temporal atrophy, drug dose and type, and living condition (Wattmo et al., 2011). However, gathering information as listed above is impractical. It remains physician's empirical judgement to predict treatment response for each individual patient.

MCI is a diagnosis when patients show subtle signs of memory or other cognitive impairment without losing independent daily-living ability. MCI is not dementia, but patients are of high risk of converting to dementia, with approximately 12% of annual conversion rate (Petersen et al., 1999). On the other hand, not all patients will convert to dementia, as roughly 80% will convert and roughly 20% will remain unchanged or revert to normal cognition (Tibuas-Pereira et al., 2016). Because of uncertain outcomes of MCI, treatment guidelines of MCI are inconsistent regarding the use of ChEI. Most guidelines do not recommend ChEI as a treatment option, but some allows clinicians to prescribe ChEI as off-label use (Petersen et al., 2018). Recent consensus of treatment strategy switches to more early stage of dementia, and MCI becomes the focus of research and development. Currently, there are only a handful of papers reporting ChEI response in MCI, and the findings are inconsistent probably due to heterogeneity of MCI (Han et al., 2019; Kasper et al., 2020).

Therefore, a method for predicting cognitive outcomes of MCI under ChEI treatment using brain age is imperatively needed.

SUMMARY OF THE INVENTION

With respect to the technical limitations in the prior art, the present disclosure provides a brain age score used to predict the severity of dementia of a person and to predict his/her dementia outcome in the following years, and the program thereof. Specifically, the brain age score is PAD, and it evaluates the current CDR of a patient as well as predicting the patient's CDR change in the next few years.

Brain age is a type of brain predicted age derived from a brain image-based machine learning method (Cole and Franke, 2017). It entails training of a brain age model using a large amount of brain images from a group of healthy people together with each individual's chronological age. Typically, features of brain structure or function are extracted from the brain MRI data and the features are trained by the machine learning algorithm. The algorithm produces a prediction model to predict an individual's chronological age based on his/her brain images, hence called brain predicted age. Once the model is trained and validated, it can then be used to estimate brain age of an individual, and the PAD, defined as the difference between brain age and chronological age of an individual, is then calculated to indicate the aging status of the brain.

PAD has been shown to be a potential cognitive aging marker. It is associated with cognitive impairment (Liem et al., 2017), fluid intelligence (Cole, 2020; Cole et al., 2018), and various cognitive abilities (Boyle et al., 2020; Richard et al., 2018). Beheshti et al. estimated PAD using individual's morphometric features extracted from T1w MRI (Beheshti et al., 2018). They found that PAD was associated with the scores of several clinical assessments of dementia including the CDR. Beheshti's work demonstrated the capability of PAD in predicting the CDR at the moment of MRI scanning, however, they did not have longitudinal data to investigate the prediction of PAD in the CDR change in the following years.

The Open Access Series of Imaging Studies (OASIS) is a databank which collects MRI and PET data, neuropsychological testing, and clinical data (https://www.oasis-brains.org/). It is publicly available to the scientific community with the aim of studying the effects of healthy aging and AD. The OASIS-3 is a dataset released in 2019 which comprises longitudinal data of 1098 participants, aged from 42 to 95 years (LaMontagne et al., 2019). The participants include (1) generally healthy and cognitively normal, i.e. the Clinical Dementia Rating (CDR)=0, individuals with or without a family history of Alzheimer's disease (AD), and (2) otherwise healthy individuals with questionable, mild, moderate or severe dementia, i.e. CDR=0.5, 1, 2, or 3, respectively. All participants gave informed consent following procedures approved by the Institutional Review Board of Washington University School of Medicine.

Being able to predict a person's CDR in the following years is of great interest for healthcare professionals and patients because appropriate intervention and follow-up visits can be prescribed individually. Therefore, the present method is based on a system of 258 cognitively normal adults in the OASIS data to build a pre-established prediction model, which is a brain age model, and applied the model to participants with different CDRs encompassing 0, 0.5 and 1 at the baseline, i.e., the time of MRI scanning, and investigated the association of PAD with the CDR change in several years of follow-up.

Specifically, the present invention establishes three conclusions. First, PADs were different among participants with different CDR scores of 0, 0.5 and 1 at the baseline. Second, PAD in participants with stable CDR of 0.5 was different from PAD in participants with the CDR of 0.5 at the baseline but turned to 0 or 1 in the follow-up. Third, PAD in participants with stable CDR of 0 was different from PAD in participants whose baseline CDR was 0 but converted to 0.5 in the follow-up years.

Moreover, instead of using morphometric features of gray matter from T1w MRI (Beheshti et al., 2018) or FW content from diffusion MRI (Maillard et al., 2019), the present invention uses microstructural features of white matter (WM) of the brain extracted from diffusion tensor imaging (DTI) to calculate PAD, dubbed WM PAD, and establishes a method which associates the WM PAD and the CDR. Specifically, an individual's WM PAD is associated with this person's concomitant CDR. In addition, given the CDR of a person, WM PAD is also associated with the CDR change in the following two to three years. This method for associating the WM PAD and the CDR allows the medical professionals to use WM PAD as a surrogate marker to predict the CDR and its future outcome in the coming years.

In another aspect, the present invention validates that brain age can predict long-term cognitive outcomes of ChEI treatment in patients with MCI. In particular, gray matter brain age was used because neurons of cholinergic pathways reside ubiquitously in gray matter of the brain including the thalamus, striatum, limbic system, and neocortex. The present invention establishes that gray matter brain age can predict cognitive decline in 2 to 3 years in patients with MCI under ChEI treatment. The present invention has compared PAD between patients with stable cognition and those with declined cognition. To control the confounding factors, the two patient groups were balanced in potential covariates of treatment response.

In one embodiment of the invention, a method and related computer based program have been designed to read the specified brain image data of an individual as inputs and estimates the person's predicted age difference (PAD), and according to the predefined cutoff value of PAD, it is determined whether the person is likely/or unlikely to be cognitively normal if he/she were assessed by the clinical dementia rating (CDR). The method and the program are used for a retrospective study on a cohort of a databank OASIS-3, and evaluated the performance of PAD in identifying patients who were likely/or unlikely to be cognitively normal (CDR=0) by comparing the results with patient's CDR scores.

In one embodiment, the current invention is directed to a method of quantitatively evaluating likelihood of a disease condition and/or condition change from a medical image of an individual's brain, the method comprising (1) processing the original medical image to obtain a first medical image and a second medical image; (2) processing the first medical image to obtain segments of at least one brain tissue of the first medical image; (3) obtaining a deformation map of the individual's brain based on the segments of at least one brain tissue obtained in the step (2); (4) correcting artifacts of the second medical image; (5) obtaining at least one diffusion-related values of the brain tissue using the artifact-corrected second medical image obtained in the step (4) and the deformation map obtained from the first medical image in the step (3); (6) calculating predicted age difference (PAD) by inputting the extracted diffusion-related values obtained in the step (5) to an established brain age prediction model; (7) predicting likelihood of a disease condition or condition change from the PAD using a disease condition or a condition change prediction model.

In one embodiment of the invention, the disease condition refers to concomitant CDR. In one embodiment, the disease condition change refers to CDR change in 2-3 years. In one embodiment, the diffusion-related values includes the fractional anisotropy (FA) and mean diffusivity (MD) values.

In another aspect of the invention, the method of quantitatively evaluating likelihood of a disease condition or condition change from a medical image of an individual's brain, wherein the first image is a T1-weighted (T1w) image.

In another aspect of the invention, the method of quantitatively evaluating likelihood of a disease condition or condition change from a medical image of an individual's brain, wherein the second image is obtained from a diffusion tensor imaging (DTI) sequence.

In another aspect of the invention, the method of quantitatively evaluating likelihood of a disease condition or condition change from a medical image of an individual's brain, wherein the at least one brain tissue includes white matter (WM), gray matter (GM), or both.

In another aspect of the invention, the method of quantitatively evaluating likelihood of a disease condition or condition change from a medical image of an individual's brain, wherein the step (3) includes registering the segments of at least one brain tissue obtained in the step (2) to MNI space.

In another aspect of the invention, the method of quantitatively evaluating likelihood of a disease condition or condition change from a medical image of an individual's brain, wherein the step (4) includes inverting T1w contrast to synthesize a pseudo b0 image and registering the DTI to pseudo b0 image to correct the artifacts of DTI data.

In another aspect of the invention, the method of quantitatively evaluating likelihood of a disease condition or condition change from a medical image of an individual's brain, wherein the brain tissue of step (5) is WM.

In another aspect of the invention, the method of quantitatively evaluating likelihood of a disease condition or condition change from a medical image of an individual's brain, wherein the diffusion-related values of step (5) include fractional anisotropy (FA) and mean diffusivity (MD).

In another aspect of the invention, the method of quantitatively evaluating likelihood of a disease condition or condition change from a medical image of an individual's brain according to any preceding claims, wherein the disease condition is the clinical dementia rating (CDR).

In another aspect of the invention, the invention is directed to a method for evaluating the clinical dementia rating (CDR) of an individual and CDR's future change from predicted age difference (PAD) based on MRI data of the individual's brain, comprising: (1) acquiring MRI data of the individual's brain using T1-weighted (T1w) imaging and diffusion tensor imaging (DTI) sequences; (2) processing the acquired T1w data so as to obtain white matter (WM) and grey matter (GM) segments; (3) registering the WM and GM segments obtained in the step (2) to the MNI space to obtain the deformation map of the individual's brain; (4) correcting artifacts of the DTI data; (5) obtaining fractional anisotropy (FA) and mean diffusivity (MD) maps for the individual in native space based on the artifact corrected DTI data; (6) extracting FA and MD values of WM region of the individual's brain using the FA and MD maps obtained in the step (5) and the deformation map obtained in the step (3); (7) calculating the WM PAD by inputting the extracted FA and MD of WM to an established brain predicted age model; (8) predicting the CDR and CDR change of the individual from the WM PAD using a CDR prediction model and a CDR change prediction model.

In another aspect of the invention, the method for estimating the clinical dementia rating (CDR) of an individual and CDR's future change from predicted age difference (PAD) based on MRI data of the individual's brain, wherein the step (2) comprising: (i) correcting SI inhomogeneity of T1w data; (ii) segmenting tissue probability maps (TPM); (iii) obtaining WM and GM segments.

In another aspect of the invention, the method for estimating the clinical dementia rating (CDR) of an individual and CDR's future change from predicted age difference (PAD) based on MRI data of the individual's brain, wherein the step (2) further comprising: inverting T1w contrast to synthesize a pseudo b0 image.

In another aspect of the invention, the method for estimating the clinical dementia rating (CDR) of an individual and CDR's future change from predicted age difference (PAD) based on MRI data of the individual's brain, wherein the step (4) comprising: registering the DTI data to pseudo b0 image to correct the artifacts of DTI data.

In another aspect of the invention, the method for estimating the clinical dementia rating (CDR) of an individual and CDR's future change from predicted age difference (PAD) based on MRI data of the individual's brain, wherein the step (5) comprising: (i) estimating diffusion tensor at each image pixel of the artifact corrected DTI data; (ii) calculating FA and MD at each pixel using a diffusion tensor indexes derived from the estimated diffusion tensor at each pixel; (iii) generating the FA and MD maps in the native space using the FA and MD at each pixel.

In another aspect of the invention, the method for estimating the clinical dementia rating (CDR) of an individual and CDR's future change from predicted age difference (PAD) based on MRI data of the individual's brain, wherein MD=$(\lambda 1+\lambda 2+\lambda 3)/3$; FA=$[3(\Delta\lambda 1^2+\Delta\lambda 2^2+\Delta\lambda 3^2)/2(\lambda 1^2+\lambda 2^2+\lambda 3^2)]^{1/2}$. $\lambda 1$, $\lambda 2$, $\lambda 3$ represent the 1st, 2nd, 3rd eigenvalues of the diffusion tensor, respectively.

In another aspect of the invention, the method for estimating the clinical dementia rating (CDR) of an individual and CDR's future change from predicted age difference (PAD) based on MRI data of the individual's brain, wherein the step (6) comprising: (i) registering the FA and MD maps to the MNI space using the deformation maps in the step (3); and (ii) masking the registered FA and MD maps with WM segments.

In another aspect of the invention, the method for estimating the clinical dementia rating (CDR) of an individual and CDR's future change from predicted age difference (PAD) based on MRI data of the individual's brain, wherein: the brain predicted age model is built by regressing the chronological age of more than one individual against FA and MD values inside the WM region using a Gaussian process regression method.

In another aspect of the invention, the method for estimating the clinical dementia rating (CDR) of an individual and CDR's future change from predicted age difference (PAD) based on MRI data of the individual's brain, wherein: the individual's brain consists of the white matter region.

In another aspect of the invention, the method for estimating the clinical dementia rating (CDR) of an individual and CDR's future change from predicted age difference (PAD) based on MRI data of the individual's brain, wherein: the CDR change is the CDR of the individual in the next 2-3 years since the date of the MRI scanning.

In another aspect of the invention, the invention is directed to a non-transitory computer readable medium storing a program causing a computer to execute a process for predicting the clinical dementia rating (CDR) of an individual and CDR's future change, the process comprising: (1) processing an original medical image to obtain a first medical image and a second medical image; (2) processing the first medical image to obtain segments of at least one brain tissue of the first medical image; (3) obtaining a deformation map of the individual's brain based on the segments of at least one brain tissue obtained in the step (2); (4) correcting artifacts of the second medical image; (5) obtaining fractional anisotropy (FA) and mean diffusivity (MD) values of the brain tissue using the artifacts-corrected second medical image obtained in the step (4) and the deformation map obtained from the first medical image in the step (3); (6) calculating predicted age difference (PAD) by inputting the extracted FA and MD obtained in the step (5) to an established dMRI-brain age model; (7) predicting likelihood of a disease condition or condition change from the PAD using a disease condition or a condition change prediction model.

In another aspect of the invention, the non-transitory computer readable medium storing a program causing a computer to execute a process for predicting the clinical dementia rating (CDR) of an individual and CDR's future change, wherein the first image is a T1-weighted (T1w) image; and the second image is a diffusion tensor imaging (DTI) sequence.

In another aspect of the invention, the non-transitory computer readable medium storing a program causing a computer to execute a process for predicting the clinical dementia rating (CDR) of an individual and CDR's future change, wherein the at least one brain tissue includes white matter (WM), gray matter (GM), or both.

In another aspect of the current invention, DWI are corrected with a novel method and/or a computer based program so as to remove and/or reduce the artefacts in the dMRI data more efficiently.

In another aspect of the invention, a method of determining and predicting a brain atrophy condition for an individual using the individual's predicted age difference (PAD) comprises acquiring at least one brain image of the individual; processing the brain image to obtain at least one feature of the brain image; generating a PAD value of the individual based on the at least one feature of the image; and determining a brain atrophy condition of the individual based on the PAD value.

In one embodiment, the at least one brain image is a brain MRI image.

In one embodiment, the brain MRI image comprises an MRI image of a gray matter region of the individual's brain.

In one embodiment, the method further comprises determining a medial temporal atrophy (MTA) score based on the PAD value.

In one embodiment, the PAD value of the individual is generated using a pre-established prediction model; and the pre-established prediction model comprises at least a brain age model.

In one embodiment, the step of processing of the medical brain image comprises at least one step of spatial normalization process.

In one embodiment, the step of processing of the medical image further comprises at least one step of feature quantification process.

In one embodiment, the method further comprises predicting the brain atrophy condition's future change based on the PAD value.

In yet another embodiment of the invention, a non-transitory computer readable medium storing a program causing a computer to execute a process for determining and predicting a brain atrophy condition for an individual using the individual's PAD comprises acquiring at least one brain image of the individual; processing the brain image to obtain at least one feature of the brain image; generating a PAD value of the individual based on the at least one feature of the image; and determining a brain atrophy condition of the individual based on the PAD value.

In one embodiment, the at least one brain image is a brain MRI image.

In one embodiment, the brain MRI image comprises an MRI image of a gray matter region of the individual's brain.

In one embodiment, the method further comprises determining a medial temporal atrophy (MTA) score based on the PAD value.

In one embodiment, the PAD value of the individual is generated using a pre-established prediction model; and the pre-established prediction model comprises at least a brain age model.

In one embodiment, the step of processing of the medical brain image comprises at least one step of spatial normalization process.

In one embodiment, the step of processing of the medical image further comprises at least one step of feature quantification process.

In one embodiment, the method further comprises predicting the brain atrophy condition's future change based on the PAD value.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIG. 19 shows the algorithm for estimating R and v.

DETAILED DESCRIPTION OF THE INVENTION

Figure 1:
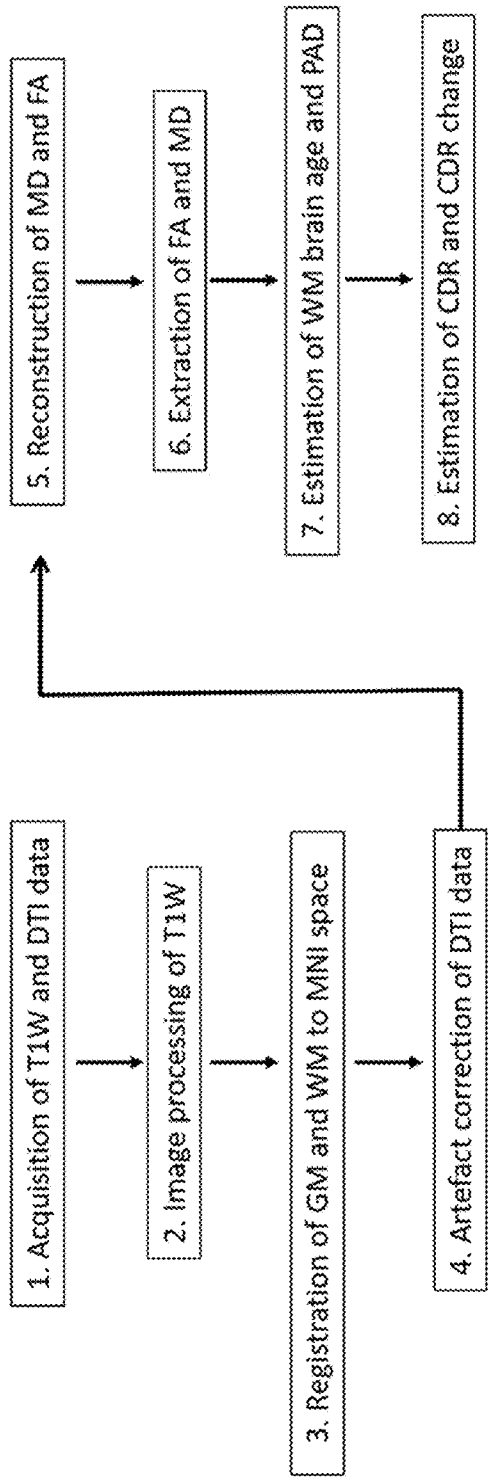
FIG. 1 shows a flow chart of a process for estimating the CDR from WM PAD.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in this disclosure, the phrase "at least one of A, B, and C" should be construed to mean a logical (A or B or C), using a non-exclusive logical OR. As used herein, the term "and/or" includes any and all combinations of one or more of the associated listed items.

Embodiments of the invention are illustrated in detail hereinafter with reference to accompanying drawings. The description below is merely illustrative in nature and is in no way intended to limit the invention, its application, or uses.

The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

The description will be made as to the embodiments of the present invention in conjunction with the accompanying drawings in FIGS. 1-20. In accordance with the purposes of this invention, as embodied and broadly described herein, this invention, in one aspect, relates to a method and related apparatus for calculating and predicting the CDR based on the MRI data of an individual's WM PAD.

FIG. 1 shows the overall flowchart of the invention: process of using WM PAD to evaluate the CDR and predict CDR change by a program. The invention starts with the acquisition of MRI data using T1w imaging and diffusion-weighted imaging sequences (step 1). To ensure the same WM component is selected from different brains, spatial registration of each individual's MRI image to a standard template in the MNI space is mandated (step 2 & 3). In one embodiment, steps 2 and/or 3 are spatial normalization process during which the MRI image such as the T1w image is segmented and the segments of certain brain tissues are registered to MNI space. Therefore, a deformation map(s) of the certain brain tissues are obtained during the spatial normalization process. To ensure accurate quantification of diffusion-weighted indexes, i.e. fractional anisotropy (FA) and mean diffusivity (MD), artefacts in the diffusion-weighted MRI data should be corrected, followed by accurate estimation of the FA and MD indexes (step 4 & 5). Having obtained the FA and MD maps in the native space and the deformation matrix between the native space and MNI space, one can transform the FA and MD maps to the MNI space and extract the FA and MD indexes within the WM component (step 6). In one embodiment, steps 5 and/or 6 are feature quantification process, during which FA and MD maps based on the artifact corrected diffusion-weighted MRI data are obtained, and FA and MD indexes of certain brain tissues are extracted. The resulting FA and MD values serve as input to an established dMRI-brain age model to estimate brain age and WM PAD (step 7). In the final step, WM PAD is used to determine the CDR and predict CDR future change using pre-established models in programs (step 8). Detailed description of each step is described as follows.

Figure 2:
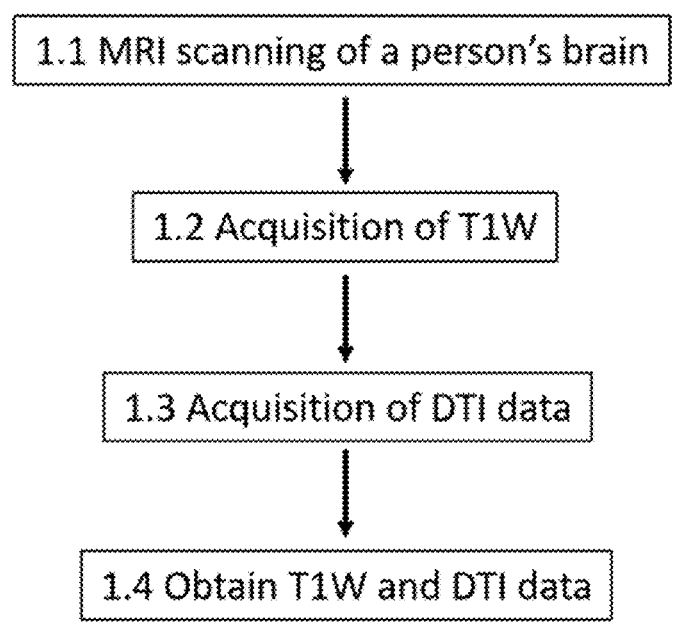
FIG. 2 shows a flow chart of a process for acquisition of T1w and DTI data.

FIG. 2 shows the process of acquisition of T1w and DTI data by the program.

Step 1.1 is MRI scanning of a person's brain. A person is scanned by a MRI system at 1.5 Tesla or 3 Tesla with a phase-arrayed multi-channel head coil. MRI scanning is contraindicated for participants who are pregnant within 1st trimester, having pacemaker or defibrillator implantation, or vascular clipping or stenting within 6 months.

Step 1.2 is acquisition of T1w. T1w data are acquired using a 3-dimensional magnetization prepared rapid gradient echo sequence. The imaging parameters are detailed as follow: repetition time (TR)=2400 ms, echo time (TE)=3.16 ms, inversion time (TI)=1000 ms, field-of-view (FOV)= 256×256×176 mm3, and matric size=256×256×176.

Step 1.3 is acquisition of DTI data. DTI data are acquired using diffusion-weighted 2-dimensional single shot spin-echo echo planar imaging using 24 different magnitudes of diffusion sensitivity (b-values) corresponding to 24 different directions (b-vectors) evenly distributed in the q space.

Step 1.4 is obtaining T1w and DTI data. In this way, one T1w data and one DTI data were obtained for each participant for the processing in step 2 and 4.

Figure 3:
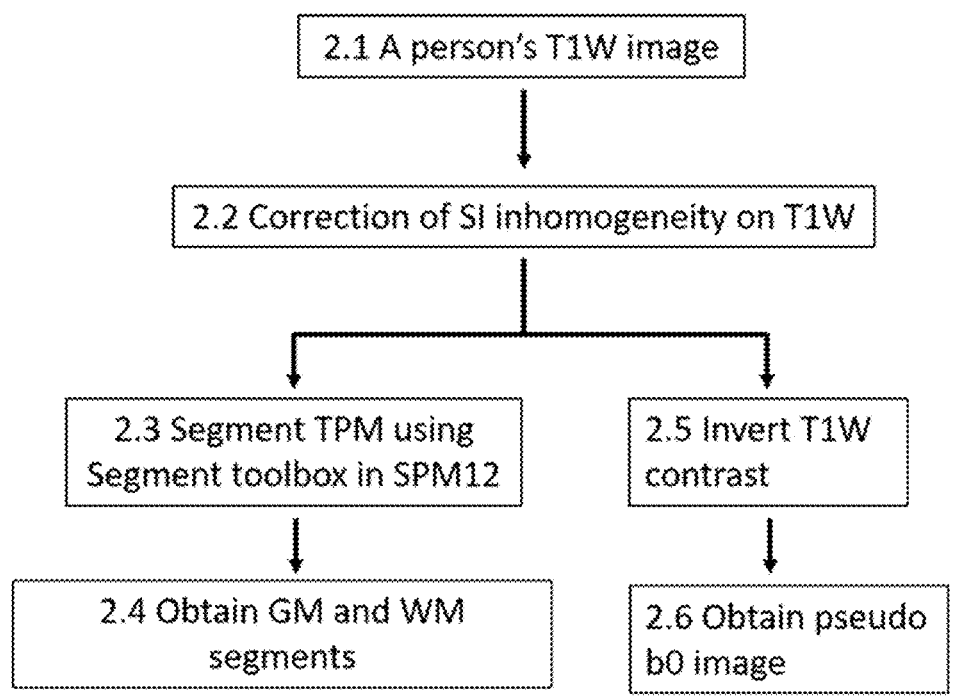
FIG. 3 shows a flow chart of a process for image processing of T1w.

FIG. 3 shows the step of image processing of T1w by the program during the spatial normalization process.

Step 2.1 is a person's T1w image. The T1w image is processed using the Segment toolbox in the SPM12 software (Wellcome Trust Centre for Neuroimaging, University College London, London, UK).

Step 2.2 is correction of SI inhomogeneity on T1w. The toolbox corrects signal intensity inhomogeneity.

Step 2.3 is segment tissue probability maps (TPM) using Segment toolbox in SPM12. Having corrected SI inhomogeneity, the toolbox segments the T1w image into various tissue segments, including gray matter (GM), white matter (WM), cerebrospinal fluid (CSF), bone, scalp, and others.

Step 2.4 is obtaining GM and WM segments. In this way, six TPMs were obtained and from which GM and WM segments are selected for the processing in step 3.

Step 2.5 is inverting T1w contrast. In parallel to step 2.3 and 2.4, the contrast of the T1w image, which has been corrected for the signal intensity inhomogeneity, is inverted to synthesize a pseudo $b_0$ image.

Step 2.6 is obtaining pseudo $b_0$ image: In this way, one obtains a pseudo $b_0$ image for each person for the processing in step 4.

Figure 4:
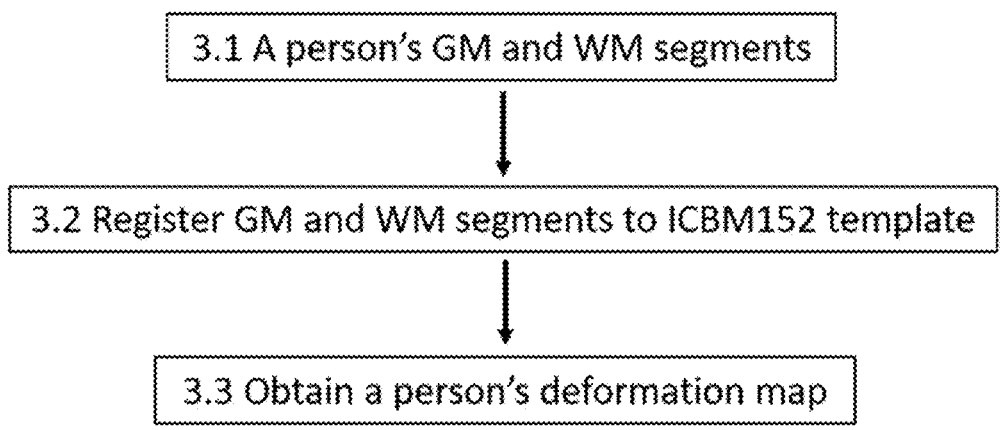
FIG. 4 shows a flow chart of a process for registration of GM and WM to MNI space.

FIG. 4 shows the process of registration of GM and WM to MNI space during the spatial normalization process.

Step 3.1 is a person's GM and WM segments. The GM and WM segments are registered to the ICBM152 template which is defined in the MNI space.

Step 3.2 is to register GM and WM segments to ICBM152 template: The registration invokes a process which is a variant of the Large Deformation Diffeomorphic Metric Mapping (LDDMM) (Beg et al., 2005; Miller et al., 2006). Specifically, the initial velocity situated in the ICBM152 space is iteratively estimated by shooting this velocity along the time dimension toward the individual's native space. In the registration, the course is divided into 10 uniform intervals, and an isotropic Gaussian filter with 10 mm full width at half maximum (FWHM) is used to ensure the smoothness of the initial velocity.

Step 3.3 is obtaining a person's deformation maps: In the final stage of convergence, a deformation map which transforms the individual's TPM to match the TPM in the ICBM152 template in obtained. The deformation map is used for the processing in step 6.

Figure 5:
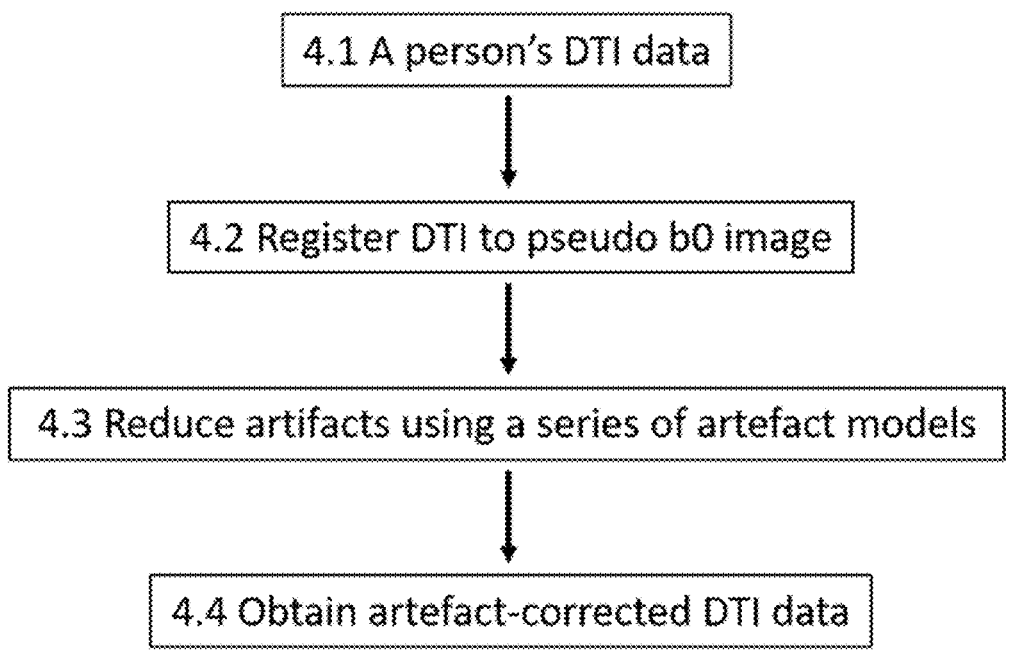
FIG. 5 shows a flow chart of a process for artifact correction of DTI data.

FIG. 5 shows the process of artifact correction of DTI data.

Step 4.1 is a person's DTI image. The raw DTI data suffers from various artefacts, including susceptibility-induced distortion, eddy current-induced distortion, head motion, and intensity inhomogeneity, which vary from person to person and should be corrected to ensure accurate registration to the MNI space.

Step 4.2 is to register DTI to pseudo $b_0$ image. The DTI data are processed using a novel registration-based method which correct these artefacts in an integrated framework. The registration-based method registers a person's raw DTI data to the same person's pseudo $b_0$ image which serves as the reference image without distortion and intensity inhomogeneity.

Step 4.3 is to reduce artifacts using a series of artefact models. By invoking the artefact models in the integrated framework, the process is able to reduce the artefacts of the DTI data.

Step 4.4 is to obtain artefact-corrected DTI image. In this way, the artefact-corrected DTI image is obtained. When the estimation achieved convergence, the corrected DTI data is also aligned with the T1w image.

Figure 6:
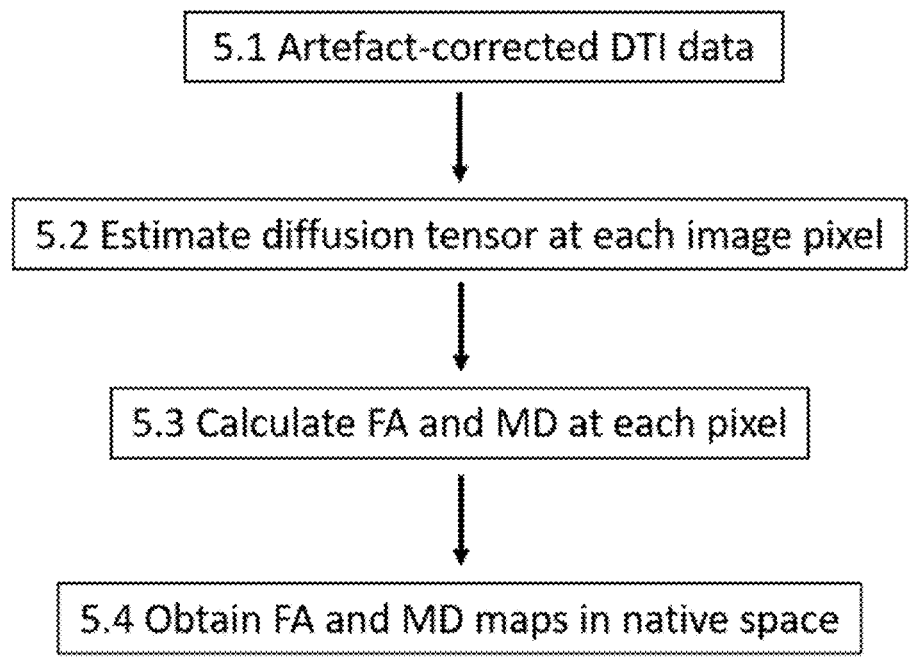
FIG. 6 shows a flow chart of a process for reconstruction of MD and FA.

FIG. 6 shows the process of reconstruction of MD and FA during the feature quantification process.

Step 5.1 is the artefact-corrected DTI data. The artefact-corrected DTI data is processed to estimate the diffusion tensor and the diffusion tensor indexes derived therein.

Step 5.2 is to estimate diffusion tensor at each image pixel. The diffusion tensor estimation is performed using an approach proposed by (Koay et al., 2007). Briefly, weighted linear least squares method is first conducted, the results are then employed as the initial estimation for the constrained nonlinear least squares method to obtain the diffusion tensors, which are ensured to be positive-definite (i.e., the eigenvalues of the diffusion tensors are all positive).

Step 5.3 is to calculate FA and MD at each pixel. The diffusion tensor indexes, i.e. fractional anisotropy (FA) and mean diffusivity (MD), are derived from the estimated diffusion tensor at each pixel. The MD and FA values are determined using the standard formula: $MD=(\lambda 1+\lambda 2+\lambda 3)/3$, and $FA=[3(\Delta\lambda 1^2+\Delta\lambda 2^2+\Delta\lambda 3^2)/2(\lambda 1^2+\lambda 2^2+\lambda 3^2)]^{1/2}$, where $\lambda 1$, $\lambda 2$ and $\lambda 3$ denoted the first, second and third eigenvalues of the diffusion tensor, respectively, and $\Delta\lambda 1$, $\Delta\lambda 2$ and $\Delta\lambda 3$ represented $\lambda 1-MD$, $\lambda 2-MD$, and $\lambda 3-MD$, respectively.

Step 5.4 is to obtain FA and MD maps in the native space: In this way, FA and MD maps for each person in native space were obtained.

Figure 7:
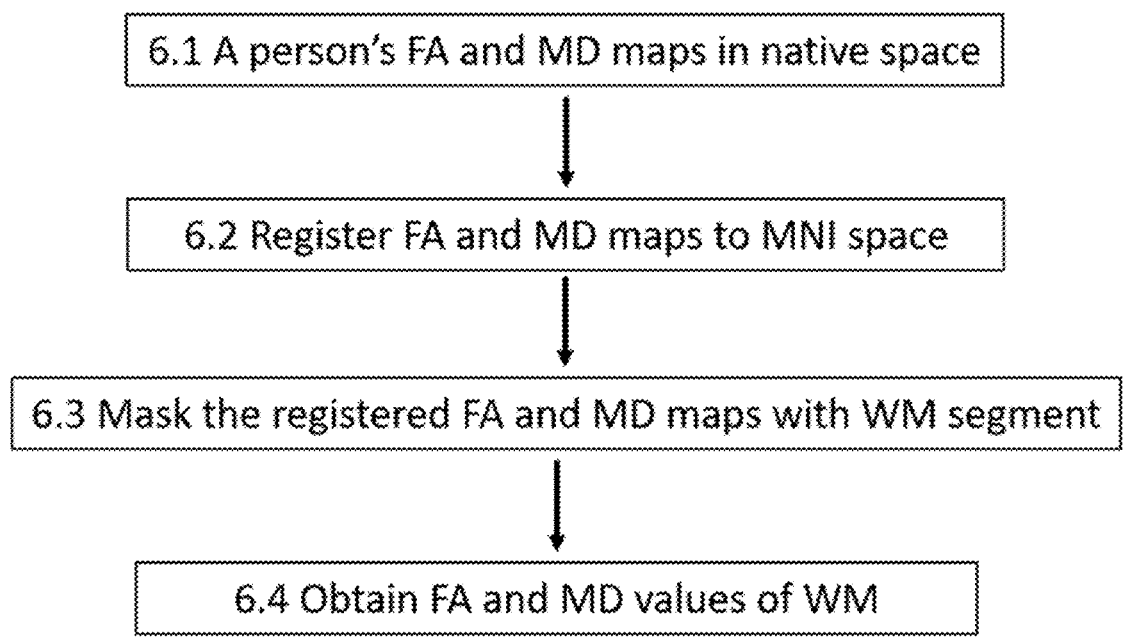
FIG. 7 shows a flow chart of a process for extraction of FA and MD.

FIG. 7 shows the process of extraction of FA and MD during the feature quantification process.

Step 6.1 is a person's FA and MD maps in native space. Having obtained the FA and MD maps in step 5, it is necessary to extract FA and MD values from the standardized WM segment.

Step 6.2 is to register FA and MD maps to MNI space. To do this, the FA and MD maps in the native space are normalized to the MNI space through the deformation map obtained in step 3.

Step 6.3 is to mask the registered FA and MD maps with WM segment. Having normalized to the MNI space, the FA and MD values in WM are masked by the standardized WM segment in the ICBM152 template.

Step 6.4 is to obtain FA and MD values of WM. In the final step, the values of FA and MD of WM for each person were obtained. The results are used for the processing in step 7.

Figure 8:
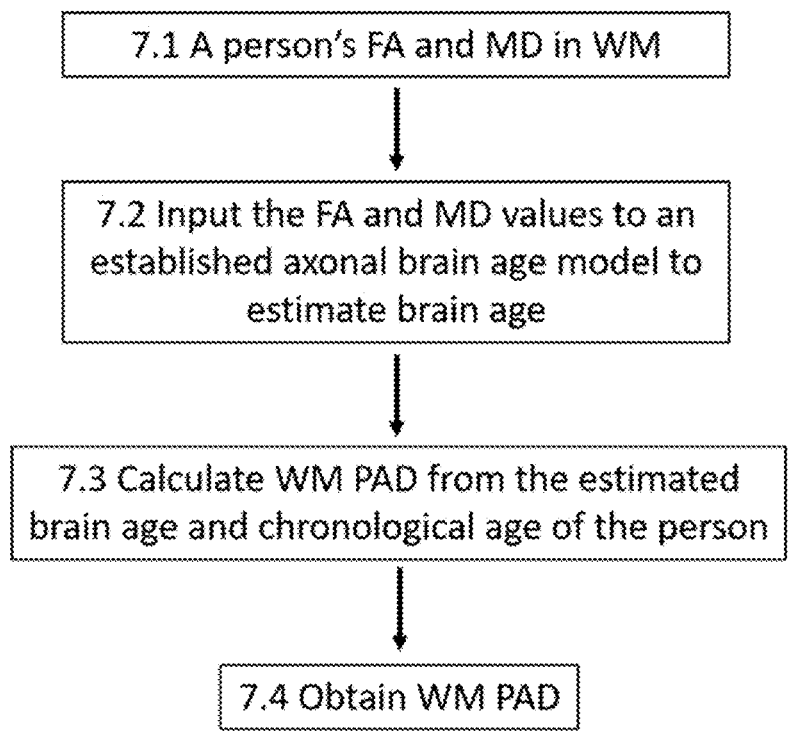
FIG. 8 shows a flow chart of a process for estimation of WM brain age and PAD.

FIG. 8 shows the process for estimation of WM brain age and PAD.

Step 7.1 is a person's FA and MD in WM: A persons' FA and MD are used as the input to an established dMRI-brain age model which was trained and validated in advance using the DTI data acquired from the same MRI scanner.

Step 7.2 is inputting the FA and MD values to an established dMRI-brain age model to estimate brain age. To build the dMRI-brain age model, a Gaussian process regression (GPR) method was used to regress the chronological age of the participants against the FA and MD values inside the WM region. The output of the model is a predicted age, called dMRI-brain age, estimated on the basis of the person's FA and MD values and the GRP model. The performance of the model has been tested and quantified in terms of the mean absolute error (MAE) and the Pearson's correlation coefficient (r) between the dMRI-brain age and chronological age.

Step 7.3 is calculating the WM PAD from the estimated brain age and chronological age of the person. Having obtained the dMRI-brain age, predicted age difference of white matter (WM PAD) is calculated by the formula: dMRI-brain age−chronological age.

Step 7.4 is obtaining WM PAD. In this way, WM PAD was obtained for estimating the CDR and CDR change.

Figure 9:
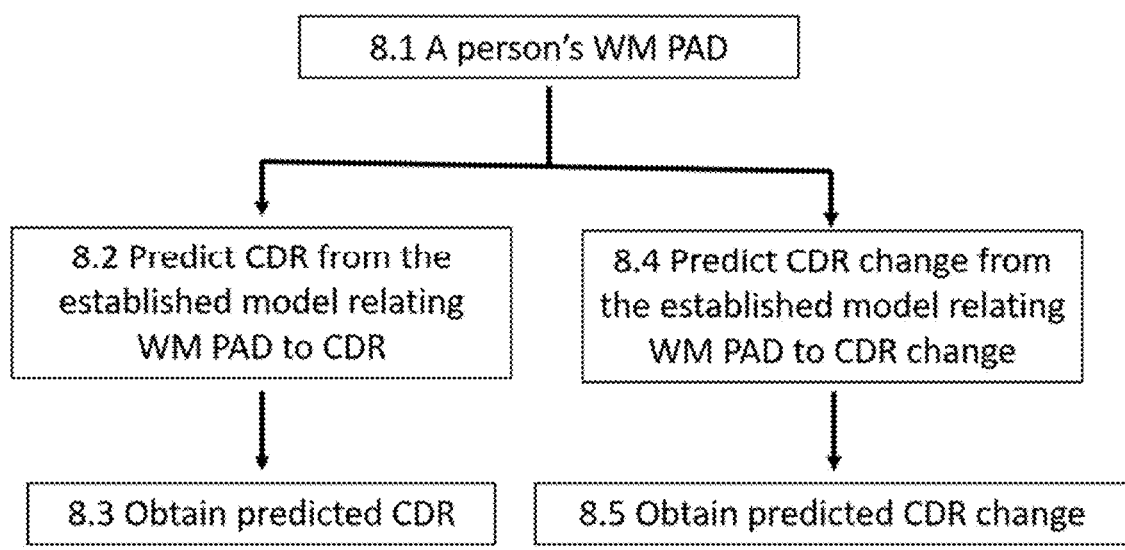
FIG. 9 shows a flow chart of a process for prediction of the CDR and CDR change.

FIG. 9 shows the process for determining of the CDR and prediction of CDR future change.

Step 8.1 is a person's WM PAD. A person's WM PAD is used as input of an established prediction model to determine his/her CDR and/or predict CDR future change.

Step 8.2 is to determine the CDR from the established model relating WM PAD to the CDR. To build the prediction model of the CDR from WM PAD, a linear regression model is applied to a dataset from a group of people whose WM PAD and concomitant CDR are known in advance. In one embodiment, the dataset from the group of people whose WM PAD and concomitant CDR are known in advance is used to establish a brain age model.

Step 8.3 is to obtain determined CDR. Using the established regression model of the CDR and/or brain age model, the CDR of a person is determined from the same person's WM PAD.

Step 8.4 is to predict the CDR future change from the established model relating WM PAD to CDR future change. To build the prediction model of the CDR future change from WM PAD, a linear regression model is applied to a dataset of a group of people whose WM PAD and the records of the CDR 2 to 3 years after WM PAD measurement are known. In one embodiment, such a model is a brain age model. The CDR change is defined as the difference between the CDR which is taken at the same time as WM PAD measurement and the CDR taken 2 to 3 years later.

Step 8.5 is to obtain predicted CDR change. Using the established regression model of the CDR change, the CDR change of a person is predicted from the same person's WM PAD.

In one embodiment, a pre-established prediction model includes both the dMRI-brain age model being used in calculating the WM PAD from the extracted FA and MD value in step 7, as well as the models relating WM PAD to the CDR and CDR change in step 8.

In one embodiment, the medical brain images of a number of patients are processed to extract at least one feature of each patient. Given a set of training data, this pre-established prediction model is constructed by associating the features with the conditions of cognitive status and/or impairment using machine-learning methods. For independent data, the model can be used to predict the conditions of cognitive status and/or impairment by inputting the brain image features.

Figure 24:
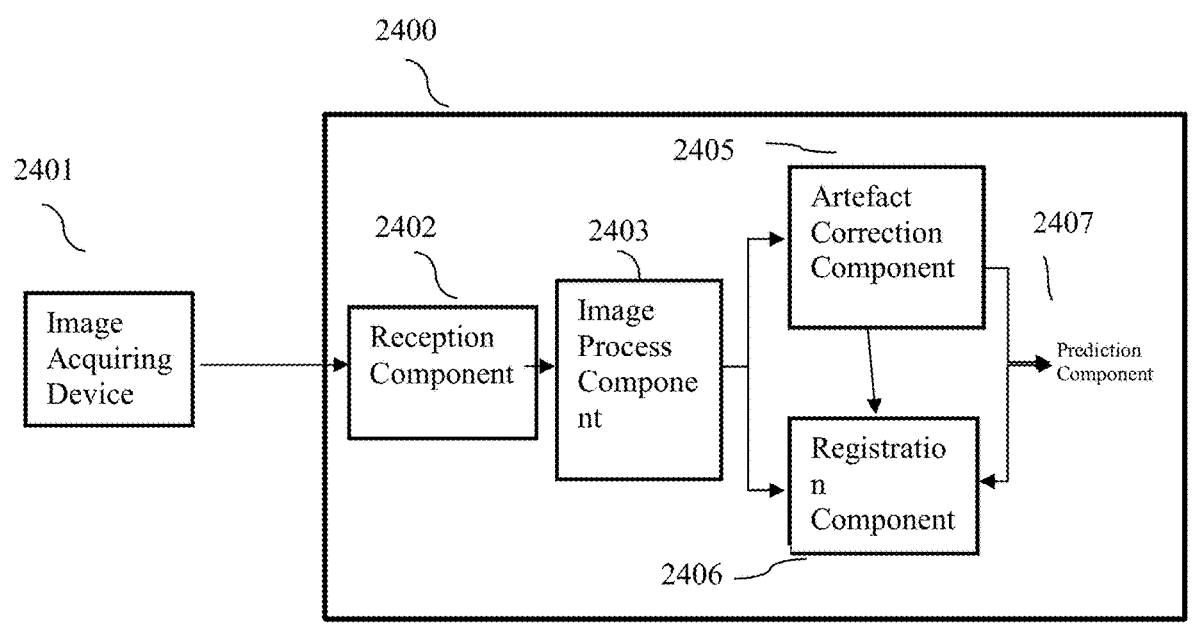
FIG. 24 shows a conceptual data flow diagram illustrating the data flow between different components/means in an exemplary apparatus.

FIG. 24 is a conceptual data flow diagram illustrating the data flow between different components/means in an exemplary apparatus 2400. In one embodiment, one or more image acquiring device (e.g. MRI scanner(s)) collect patient's brain image data and transmits the data to a reception component 2402 for being further processing. The reception component 2402 then transmits the image data to an image process component 2403. It should be noted that in other embodiment, the image acquiring device(s), may directly transmit the image data to the image process component 2403, without using the reception component 2402.

The image process component 2403 processes the steps 2.1-2.6 to obtain pseudo $b_0$ image and GM and WM segments information. It then transmits the GM and WM segments information to a registration component 2406 for step 3.1-3.3 to obtain the deformation map. In parallel, the pseudo $b_0$ image information and DTI data were transmitted to an artefact correction component 2405 for step 4.1-4.4, during which the artefact-corrected DTI image is obtained.

In one embodiment, a prediction component 2407 then receives the deformation map from the registration component 2406, and artefact-corrected DTI data from the artefact correction component 2405. The prediction component 2407 may then proceed steps 5-8. In another embodiment, the steps 6.1-6.4 may take place at the registration component 2406 for obtaining FA and MD values of WM.

Figure 25:
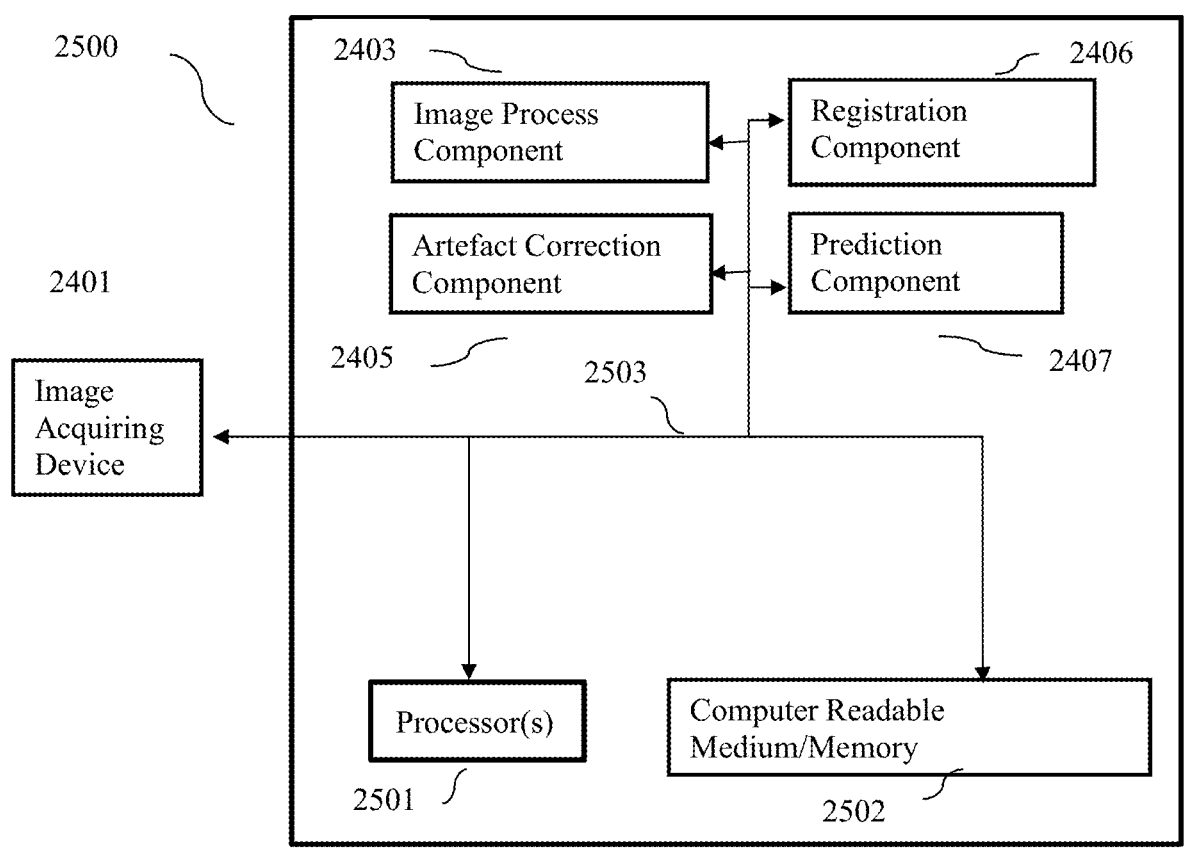
FIG. 25 shows a diagram illustrating an example of a hardware implementation for an apparatus employing a processing system.

FIG. 25 is a diagram 2500 illustrating an example of a hardware implementation for a processing system 2400. The processing system 2500 may be implemented with a bus architecture, represented generally by a bus 2503. The bus 2503 may include any number of interconnecting buses and bridges depending on the specific application of the processing system 2500 and the overall design constraints. The bus 2503 links together various circuits including one or more processors and/or hardware components, represented by one or more processors 2501, the image process component 2403, the artefact correction component 2405, the registration component 2406, the prediction component 2407, and a computer-readable medium/memory 2502. The bus 2503 may also link various other circuits such as timing sources, peripherals, voltage regulators, and power management circuits, etc.

The processing system 2500 may be coupled to an image acquiring device 2401, which may be a MRI scanner or other clinical image acquiring device.

The processing system 2500 includes one or more processors 2501 coupled to a computer-readable medium/memory 2502. The one or more processors 2501 are responsible for general processing, including the execution of software stored on the computer-readable medium/memory 2502. The software, when executed by the one or more processors 2501, causes the processing system 2500 to perform the various functions described supra for any particular apparatus. The computer-readable medium/memory 2502 may also be used for storing data that is manipulated by the one or more processors 2501 when executing software. The processing system 2500 further includes at least one of the image process component 2403, the artefact correction component 2405, the registration component 2406, the prediction component 2407. The components may be software components running in the one or more processors 2501, resident/stored in the computer readable medium/memory 2502, one or more hardware components coupled to the one or more processors 2501, or some combination thereof.

It is understood that the specific order or hierarchy of blocks in the processes/flowcharts disclosed is an illustration of exemplary approaches. Based upon design preferences, it is understood that the specific order or hierarchy of blocks in the processes/flowcharts may be rearranged. Further, some blocks may be combined or omitted. The accompanying method claims present elements of the various blocks in a sample order, and are not meant to be limited to the specific order or hierarchy presented.

Example 1

This artifact correction steps 4.1-4.3 and FIG. 5 is presented in a more detailed manner in FIG. 14-20.

Figure 14:
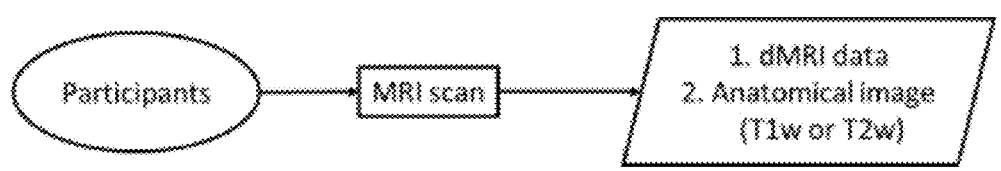
FIG. 14 shows the process for participant's brain being scanned by an MRI scanner.
Figure 15:
FIG. 15 shows the process for the anatomical image being converted to the pseudo $b_0$ image.
Figure 16:
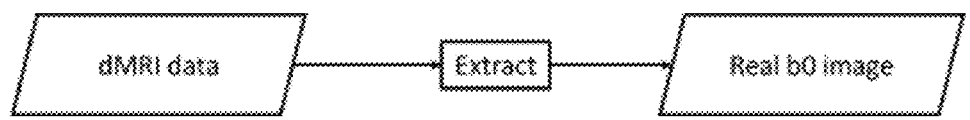
FIG. 16 shows the process for extracting the real $b_0$ image from the dMRI data.
Figure 17:
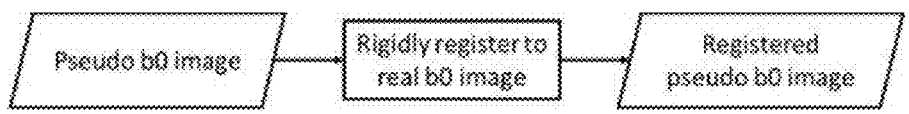
FIG. 17 shows the process the pseudo $b_0$ image is rigidly registered to the real $b_0$ image.

In particular, the participant's brain is scanned by a MRI scanner. The dMRI data and the anatomical image (T1w or T2w) are acquired. (FIG. 14.) The anatomical image is converted to the pseudo $b_0$ image, which has similar image contrast to the real $b_0$ image. (FIG. 15) The real $b_0$ image is extracted from the dMRI data. (FIG. 16) The pseudo $b_0$ image is rigidly registered to the real $b_0$ image. This registered image is denoted as $f_0:\Omega \to \mathbb{R}^+ f_0:\Omega \to \mathbb{R}^+$ and the real $b_0 b_0$ image is $f_1:\Omega \to \mathbb{R}^+ f_1:\Omega \to \mathbb{R}^+$. Here $\Omega \subset \mathbb{R}^3 \Omega \subset \mathbb{R}^3$ denotes the image domain. The coordinate of $f_0 f_0$ is $r \in \Omega r \in \Omega$. The PE direction of $f_1 f_1$ is $p \in \mathbb{S}^2 p \in \mathbb{S}^2$. (FIG. 17)

It is assumed that the bias field is multiplicative and model it with $e^\beta$, where $\beta:\Omega \to \mathbb{R}$. In this way, $f_0 = e^\beta \cdot f_0$ would be similar to $f_1$. The smoothness of the $\beta$ field is achieved via differential operator $L_\beta$, with the norm of $\beta$ defined as $\|\beta\|^2 = \langle l_\beta \beta | \beta \rangle_2$. According to FIG. 18, $\psi=\Omega \to R$ is used to denote the field map (in unit of Hz). The relation between the distortion map and the field map is $$\varphi(r) = r + k \cdot \psi(\gamma) \cdot p, \forall r \in \Omega \tag{1}$$

where $k=\tau V$, $\tau$ is the effective echo-spacing time and V is the filed of view if the DW image in the PE direction. Let $v=k\psi$ be the initial velocity. The smoothness of v is achieved via differential operator $L_v$, with the norm of v defined as $$\|v\|^2 = \langle l_v v | v \rangle_2$$

Figure 18:
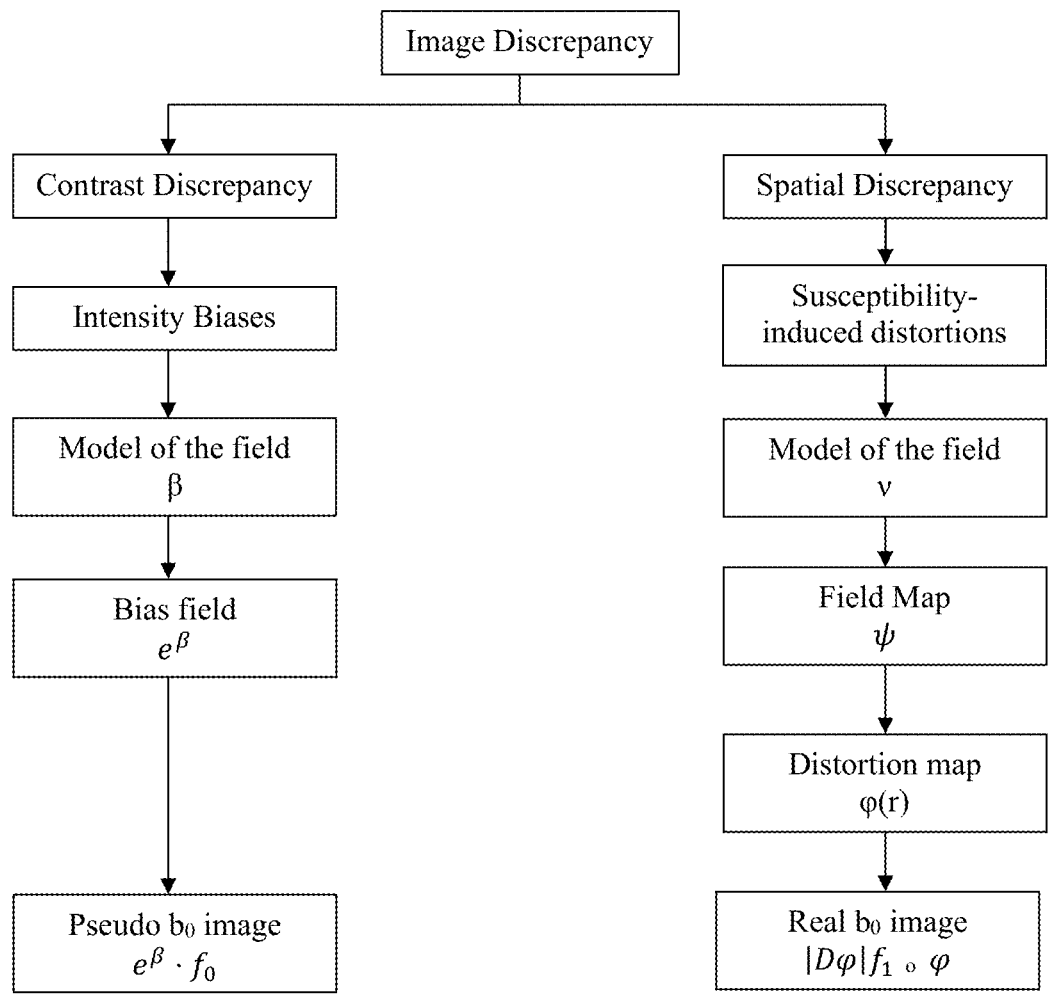
FIG. 18 shows the image discrepancy modeling.

The distortion corrected image is $|D\varphi| f_1 \circ \varphi$, where $\circ$ denotes function composition. (FIG. 18)

FIG. 19 shows the process to estimate $\beta$ and v. The cost function to be minimized is $E_1 = E_d + E_\beta + E_v$, where $$Ed = \frac{1}{2}\sigma d \int_{r \in \Omega} |D^\varphi|^{-1}(e^\beta f_0 - |D\varphi| f_1^0 \varphi)^2 dr \tag{2}$$

$$Ed = \frac{1}{2}\sigma d \|l_\beta \beta\|^2$$

$$Ev = \frac{1}{2}\sigma v \|l_v v\|^2$$

The present invention uses the sum of squared differences (SSD) to quantify the data-matching between the real and pseudo $b_0$ images ($E_d$), with the regularizations penalizing non-smooth bias field ($E_\beta$) and non-smooth initial velocity ($E_v$). Parameters $\sigma_d$, $\sigma_\beta$, and $\sigma_v$ are the weightings for the data-matching and the regularization terms, respectively.

For notational convenience, the present invention defines some assistant functions. The function b=vec(A) converts the 3D field A: $\Omega \to \mathbb{R}$ to the vector $b \in R^{n_{xyz} \times 1}$ by concatenating the field column by column, where $n_{xyz}$ is the total number of voxels. The reverse operation is achieved by A=ivec(b). In addition, the function B=diag(b) converts the b vector to the diagonal matrix B.

The Gauss-Newton approach is used to update the values of $\beta$. Let $$g\beta = |D^\varphi|^{-1} e^\beta f_0 (e^\beta f_0 - |D\varphi| f_1^0 \varphi) \tag{3}$$

$$H\beta = 2|D^\varphi|^{-1}(e^\beta f_0)^2$$

And $b_\beta$=vec($\beta$), $g_\beta$=vec($g_\beta$), and $H_\beta$=diag(vec($H_\beta$)), The descent deviation is computed via $$\delta b_\beta = (\sigma_d H_\beta + L_\beta)^{-1}(\sigma_d g_\beta + \sigma_\beta L_\beta b_\beta) \tag{4}$$

or in the 3D field form $\delta\beta$=ivec($\delta b_\beta$), then the $\beta$ field is updated by $$\beta^{(iter+1)} = \beta^{(iter)} - \gamma\beta \cdot \delta\beta^{(iter)} \tag{5}$$

Where $0 < \gamma_\beta \leq 1$ is a scaling factor controlling the descent size. The differential operator $L_\beta$ is implemented through $$\langle l_\beta \beta | \beta \rangle_2 = \int_{r \in \Omega} \lambda_{\beta,1} \|\nabla \beta(r)\|^2 + \lambda_{\beta,2} \|\nabla^2 \beta(r)\|^2 dr, \tag{6}$$

where the first term in the integral is the membrane energy and the second is the bending energy, $\lambda_{\beta,1}$ and $\lambda_{\beta,2}$ control their strength of regularization, respectively. Practically, this differential operator is expressed in the matrix form $L_\beta \in R^{n_{xyz} \times n_{xyz}}$. Same as the bias field, Gauss-Newton approach is used to update the initial velocity field v. Let $$gv = e^\beta f_0 \nabla_p (|D^\varphi|^{-1}(e^\beta f_0 - |D\varphi| f_1^0 \varphi)) \tag{7}$$

$$Hv = |D^\varphi|^2 \nabla_p (|D^\varphi|^{-1} e^\beta f_0) \cdot \nabla_p^T (|D^\varphi|^{-1} e^\beta f_0)$$

Here $\nabla_p$ is the gradient along the p direction. Also let $b_\beta$=vec($\beta$), $g_\beta$=vec($g_\beta$), and $H_\beta$=diag(vec($H_\beta$)), the descent deviation is computed via $$\delta b_v = (\sigma_d H_v + L_v)^{-1}(\sigma_d g_v + \sigma_v L_v b_v) \tag{8}$$

or in the 3D field form $\delta v$=ivec($\delta b_v$), then the v field is updated by $$v^{(iter+1)} = v^{(iter)} - \gamma v \cdot \delta v^{(iter)} \tag{9}$$

where $0 < \gamma_v \leq 1$ controls the descent size. The differential operator $L_v$ is defined with the same form as $L_\beta$, where the strength of membrane energy and that of bending energy are controlled by $\lambda_{v,1}$ and $\lambda_{v,2}$, respectively. This differential operator is encoded in the matrix $L_v \in R^{n_{xyz} \times n_{xyz}}$.

Compare to existing method, the current registration method is dedicated for the susceptibility-induced distortions, which is a 1D deformation along the PE direction. While the first derivative ($g_v$) has been shown previously, the Hessian ($H_v$) which is an approximation to the second derivative is our invention. Therefore, this method estimates the field map using a Gauss-Newton optimization scheme, which is more efficient as compared to existing methods.

Moreover, a term called "bias field" is introduced to model the contrast discrepancy between the real $b_0$ image and the pseudo $b_0$ image. Existing anatomical image-base methods do not explicitly consider the contrast discrepancy in the estimation procedures.

Figure 20:
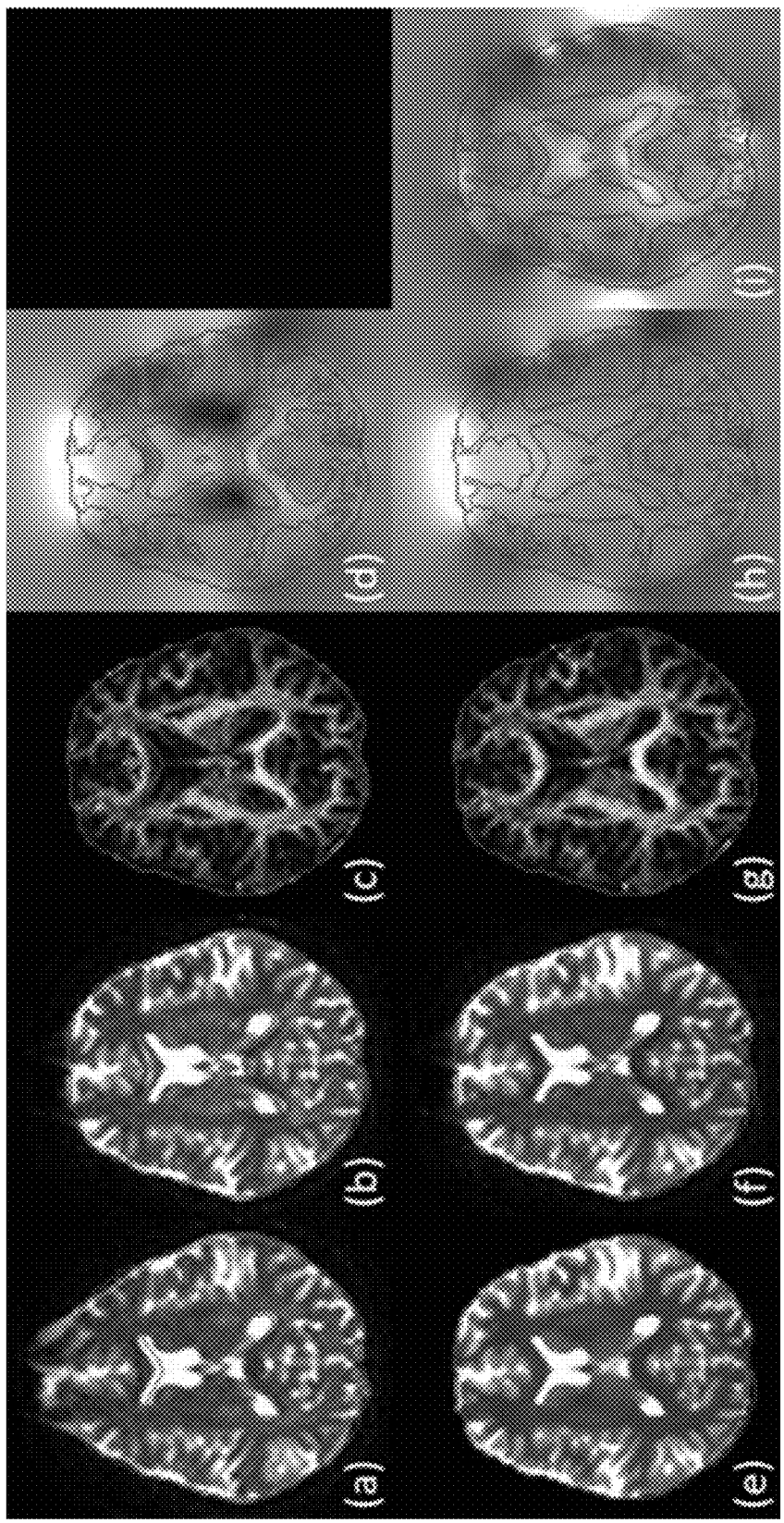
FIG. 20 shows the results of correcting the artefacts of a participant's dMRI data.

FIG. 20 shows an example of using the proposed method. As it can be observed, the raw $b_0$ image (FIG. 20(a)) suffers from large distortions around the frontal regions, with reference to the pseudo $b_0$ image (FIG. 20(e)). If the artefact models do not take the intensity biases into consideration, the method falls into local minima, rendering the distortions not adequately corrected, such as those regions indicated by the green arrows in the $b_0$ image (FIG. 20(b)) and the fractional anisotropy (FA) map (FIG. 20(c)). On the other hand, using the bias field (FIG. 20(i)) to model the intensity biases can result in a proper registration, hence the $b_0$ image (FIG. 20(f)) and the FA map (FIG. 20(g)) aligned to the pseudo $b_0$ image very well. The field map estimated using the model with intensity biases (FIG. 20(h)) is much smoother than that without (FIG. 20(d)). An explanation to the results is the locally large image discrepancy between the real and pseudo $b_0$ images. Recall that two primary sources contribute to the image discrepancy: spatial discrepancy (by susceptibility-induced distortions) and the contrast discrepancy (by intensity biases). If the algorithm disregards the contribution of the intensity biases, the algorithm would attempt to reduce the cost function (i.e., SSD) by spatially aligning the registered images. It is well known that registration, particularly non-linear, is an ill-posed problem. In this manner, registering regions with large intensity biases is easy to result in wrong point-by-point correspondence and wrong field map.

The results reveal that (1) the estimated field map could adequately correct the susceptibility-induced distortions, and (2) modeling the intensity biases could facilitate the correction for the susceptibility-induced distortions.

Example 2

Method
1. Subjects

The participants in OASIS-3 were enrolled by different projects related to Knight ADRC. The participants were (1) generally healthy and cognitively normal (CDR=0) individuals with or without a family history of AD, and (2) generally healthy individuals with CDR=0.5, 1 or 2. The exclusion criteria included medical conditions that precluded longitudinal participation, e.g. end-stage renal disease requiring dialysis or contraindications for the MRI study, e.g. pacemaker implantation. All participants gave informed consent following procedures approved by the Institutional Review Board of Washington University School of Medicine.

2. Data Selection

Participants in OASIS-3 undertook one to multiple sessions of brain MRI scanning on three 3T MRI scanners (Siemens, Erlangen, Germany) including two scanner models, i.e., Biograph and TIM Trio. To reduce scanner-wise variability, MRI data acquired from the same scanner model (TIM Trio) using the same acquisition scheme for T1w imaging and diffusion tensor imaging (DTI) were selected for the analysis. Since the analysis required acceptable image quality of T1w and DTI data, participants whose images presented severe image artefact such as motion blurring on T1w or failed artefact correction on DTI were excluded. Consequently, a total of 529 participants in 575 MRI scanning sessions were enrolled for subsequent analysis.

3. MRI Data Acquisition

As presented above in FIG. 2 and related description, T1w data were acquired using the 3-dimensional magnetization prepared rapid gradient echo sequence. The imaging parameters were detailed as follow: repetition time (TR)=2400 ms, echo time (TE)=3.16 ms, inversion time (TI)=1000 ms, field-of-view (FOV)=256×256×176 mm3, and matric size=256×256×176. DTI data were acquired using diffusion-weighted 2-dimensional single shot spin-echo echo planar imaging using 24 different magnitudes of diffusion sensitivity (b-values) corresponding to 24 different directions (b-vectors), repeated twice. The b-values and b-vectors are listed in the Supplementary File 1. The imaging parameters were described as follow: TR=14500 ms, TE=112 ms, FOV=224×224 mm$^2$, matric size=112×112, slice thickness=2 mm. The two DTI acquisitions were concatenated to form a single DTI dataset, and so there were one T1w data and one DTI data in each MR session for each participant.

4. Image Processing

All MRI data were processed following the procedures described below. It entailed tissue segmentation, artefact correction, diffusion tensor estimation, image registration and diffusion index extraction.

4.1 As presented in FIG. 3 and related description, for brain segmentation on T1w image, the T1w image was processed using the Segment toolbox in the SPM12 software (Wellcome Trust Centre for Neuroimaging, University College London, London, UK). The toolbox corrected signal intensity inhomogeneity and segmented the T1w image into various tissue components, including gray matter (GM), white matter (WM), cerebrospinal fluid (CSF), bone, scalp, and others. The outputs of the Segment toolbox were six TPMs, each represented a brain tissue component, and the T1w image with intensity inhomogeneity being corrected. The corrected T1w image were used in the subsequent artefact correction on DTI data, and the TPMs of GM and WM were used for spatial normalization of the images to the MNI space.

4.2 Artefact correction on DTI data: As presented in FIG. 5 and related description, the raw DTI data suffered from various artefacts, including susceptibility-induced distortion, eddy current-induced distortion, head motion, and intensity inhomogeneity. The DTI data was processed using a novel registration-based process which corrected these artefacts in an integrated framework. Briefly, this process registered the raw DTI data to a pseudo $b_0$ image which was synthesized by inverting the contrast of the T1w image, intensity inhomogeneity of which had been corrected in the step 4.1. In this manner, the pseudo $b_0$ image served as the reference image without distortion and intensity inhomogeneity. By incorporating the artefact models in an integrated framework, the process was able to reduce the artefacts of the DTI data. Meanwhile, the corrected DTI data was readily aligned with the space of T1w image when the estimation achieved convergence.

4.3 Diffusion tensor estimation: According to FIG. 6, the artefact-corrected DTI data was processed to estimate the diffusion tensor using the approach proposed by (Koay et al., 2007). Briefly, the weighted linear least squares method was first conducted, the results were then employed as the initial estimation for the constrained nonlinear least squares method to obtain the diffusion tensors, which were ensured to be positive-definite (i.e., the eigenvalues of the diffusion tensors were all positive). The associated fractional anisotropy (FA) and mean diffusivity (MD) were derived from the estimated diffusion tensor at each pixel. The MD and FA values were determined using the standard formula: MD=$(\lambda 1+\lambda 2+\lambda 3)/3$, and FA=$[3(\Delta\lambda 1^2+\Delta\lambda 2^2+\Delta\lambda 3^2)/2(\lambda 1^2+\lambda 2^2+\lambda 3^2)]^{1/2}$, where $\lambda 1$, $\lambda 2$ and $\lambda 3$ denoted the first, second and third eigenvalues of the diffusion tensor, respectively, and $\Delta\lambda 1$, $\Delta\lambda 2$ and $\Delta\lambda 3$ represented $\lambda 1$–MD, $\lambda 2$–MD, and $\lambda 3$–MD, respectively.

4.4 Spatial normalization to the MNI space: The TPMs of GM and WM, segmented from the T1w image, were registered to the ICBM152 template (defined in the MNI space) using a variant of the Large Deformation Diffeomorphic Metric Mapping (LDDMM) algorithm (Hsu et al., 2012, Hsu et al., 2015, Beg et al., 2005; Miller et al., 2006). Specifically, the initial velocity situated in the ICBM152 space was iteratively estimated by shooting this velocity along the time dimension toward the individual's native space. On convergence, the associated deformation map could transform the individual's TPMs to match the ICBM152 TPM template. In the registration, the course was divided into 10 uniform intervals, and an isotropic Gaussian filter with 10 mm full width at half maximum (FWHM) was used to ensure the smoothness of the initial velocity.

4.5 Diffusion index extraction: The FA and MD maps in the native space were normalized to the MNI space through the deformation map derived from the LDDMM registration. The FA and MD values in the WM pixels were extracted using the mask created from the WM TPM of the ICBM152 template. Since FA and MD were DTI indices representing white matter microstructural property, these values were used as the features in modeling the dMRI-brain age.

All the image processing procedures were conducted using in-house programs in MATLAB (The MathWorks, Inc., Natick, MA, USA) except the brain segmentation on T1w image for which SPM12 was used.

5. Grouping According to CDR Track Records

The participants enrolled in the study were grouped into 9 groups according to the track records of their CDR values. The 9 groups were named as follow: [CN]-Modeling, [CN1]-to-CN2, CN1-to-[CN2], [CN]-to-D1, D1-to-[CN], [D1]-to-CN, [nD1], [D1]-to-D2, and [nD2]. All groups were mutually exclusive except [CN1]-to-CN2 and CN1-to-[CN2] which recruited the same participants, undertaking the first and second MRI scanning, respectively. The characteristics of the 9 groups were described below. There were 475 people included in the analysis after grouping, 258 participants in the CN-Modeling group and 217 participants in the rest of the groups.

5.1 [CN]-Modeling

This group comprised participants who were cognitively normal (CDR=0, CN for short) and stable. The CDR was 0 in all clinical records and had at least one such record within 1 year before or after the MRI scanning. The data in this group served as the training data to build the dMRI-brain age model. [CN] denoted the cognitive status of CN around the time of MR scanning.

5.2 [CN1]-to-CN2

This group comprised 46 participants who were cognitively normal and stable. The screening criteria were the same as the [CN]-Modeling group. The data in this group served as the testing data of the dMRI-brain age modeling. [CN1] denoted that the participants were CN around the time of the first MR scanning.

5.3 CN1-to-[CN2]

Participants in this group (N=46) were the same participants as those in [CN1]-to-CN2. As described above, the MRI scanning date in this group was later than that in [CN1]-to-CN2 with the inter-scan interval of 2.91±0.67 years. [CN2] denoted that the participants were CN around the time of the second MR scanning.

5.4 [CN]-to-D1

Participants in this group (N=34) were cognitively normal within the interval of 180 days from the date of MRI scanning but converted to very mild symptomatic AD (CDR=0.5, D1 for short) after the interval.

5.5 D1-to-[CN]

Participants in this group (N=25) were cognitively normal within the interval of 180 days from the MRI scanning date but were in D1 before the interval.

5.6 [D1]-to-CN

Participants in this group (N=26) were in D1 within the interval of 180 days from the MRI scanning date but turned to CN after the interval. [D1] denoted the cognitive status of D1 around the time of MRI scanning.

5.7 [nD1]

Participants in this group (N=34) were in D1 within the interval of 180 days from the MRI scanning date. After the interval, 19 participants had at least one clinical record showing that they stayed in the D1 stage, while rest of the participants (N=15) did not have any record of the CDR available. Therefore, nominal D1 (nD1 for short) was named for this group. [nD1] denoted that the participants were in nominal D1 around the time of MRI scanning.

5.8 [D1]-to-D2

Participants in this group (N=28) were in D1 within the interval of 180 days from the MRI scanning date but converted to mild symptomatic AD (CDR=1, D2 for short) after the interval.

5.9 [nD2]

Participants in this group (N=24) were in D2 within the interval of 180 days from the MRI scanning date. After the interval, 13 participants converted to moderate symptomatic AD (CDR=2, D3 for short), 6 participants had at least one clinical record showing that they stayed unchanged, and 5 participants did not have any CDR record. Therefore, nominal D2 (nD2 for short) was named for this group. [nD2] denoted that the participants were in nominal D2 around the time of MRI scanning.

Table 1 lists the demographics of the people in the analysis and Table 2 summarizes the statistical results of the pairwise comparison among the seven groups.

TABLE 1

| | | | | Demographics | | | | | | | |
|---|---|---|---|---|---|---|---|---|---|---|---|
| Group | Category | Elapsed Time (years) | Sample Size | Gender | | Age (years) | MMSE | CDR (sum of box) | Education (years) | APOE e4‡ | PAD (years) |
| | | | | Female | Male | | | | | | |
| [CN]-Modeling | Training Data | | 258 | 57.8% | 42.2% | 68.54 ± 8.75 | 29.24 + 1.17 | 0.01 + 0.06 | 16.22 ± 2.47 | 31.9% | |
| [CN1]-to-CN2 | Testing Data | 2.91 ± 0.67† | 46 | 65.2% | 34.8% | 66.19 ± 8.13 | 29.17 ± 0.93 | 0.00 ± 0.00 | 16.13 ± 2.60 | 34.8% | −0.86 ± 5.48 |
| CN1-to-[CN2] | Statistical Analysis | 2,91 + 0.67† | 46 | 65.2% | 34.8% | 69.10 + 7.86 | 29.09 + 1.15 | 0.00 + 0.00 | 16.13 + 2.60 | 34.8% | −0.75 + 5.53 |

TABLE 1-continued

Demographics

| Group | Category | Elapsed Time (years) | Sample Size | Gender Female | Gender Male | Age (years) | MMSE | CDR (sum of box) | Education (years) | APOE e4‡ | PAD (years) |
|---|---|---|---|---|---|---|---|---|---|---|---|
| [CN]-to-D1 | Statistical Analysis | 2.49 + 1.17 | 34 | 50.0% | 50.0% | 75.51 ± 6.45 | 28.85 ± 1.42 | 0.04 ± 0.14 | 15.41 ± 2.70 | 38.2% | 3.10 ± 7.72 |
| D1-to-[CN] | Statistical Analysis | 3.06 + 1.87 | 25 | 60.0% | 40.0% | 75.75 + 8.27 | 29.08 + 1.04 | 0.00 + 0.00 | 16.08 + 2.80 | 36.0% | 2.90 + 7.19 |
| [D1]-to-CN | Statistical Analysis | 1.44 ± 0.58 | 26 | 38.5% | 61.5% | 74.87 ± 7.29 | 28.35 ± 1.57 | 0.94 ± 0.59 | 15.27 ± 2.44 | 42.3% | 2.99 ± 7.16 |
| (nD1) | Statistical Analysis |  | 34 | 50.0% | 50.0% | 76.23 ± 7.21 | 26.65 + 2.91 | 1.91 + 0.97 | 14.91 + 3.39 | 52.9% | 5.48 + 6.68 |
| [D1]-to-D2 | Statistical Analysis | 2.18 + 1.06 | 28 | 32.1% | 67.9% | 75.45 ± 6.20 | 25.71 ± 2.45 | 2.45 ± 1.07 | 15.29 ± 3.09 | 57.1% | 9.21 ± 6.14 |
| (nD2) | Statistical Analysis |  | 24 | 33.3% | 66.7% | 76.40 ± 10.31 | 21.13 + 3.89 | 5.46 + 1.11 | 13.71 + 2.93 | 54.2% | 12.33 ± 10.89 |

MMSE: Mini-Mental State Examination;
CDR: Clinical Dementia Rating;
CN: CDR = 0 (Cognitively Normal);
D1: CDR = 0.5;
D2: CDR = 1;
PAD: Predicted Age Difference.
†The elapsed time here represents the inter-scan interval between [CN1]-to-CN2 and CN1-to-[CN2].
‡APOE e4 means the percentage in the group population that poses either one or two e4 alleles.

TABLE 2

Adjusted p-value of pairwise comparison (two sample t-test; adjusted for multiple comparisons using the Benjamini-Hochberg method)

| Comparison | Name of Group 1 | PAD of Group 1 (years) | Name of Group 2 | PAD of Group 2 (years) | Original p-value | Adjusted p-value | Significant (FDR of 0.05) |
|---|---|---|---|---|---|---|---|
| 1 | CN1-t-(CN2) | −0.75 + 5.53 | [CN]-to-D1 | 3.10 ± 7.72 | 0.0112 | 0.0213 | Yes |
| 2 | CN1-to-[CN2] | −0.75 ± 5.53 | D1-to-[CN] | 2.90 ± 7.19 | 0.0197 | 0.0318 | Yes |
| 3 | CN1-to-[CN2] | −0.75 ± 5.53 | [D1]-to-CN | 2.99 ± 7.16 | 0.0158 | 0.0276 | Yes |
| 4 | CN1-to-[CN2] | −0.75 ± 5.53 | [nD1] | 5.48 ± 6.68 | 0.0000 | 0.0001 | Yes |
| 5 | CN1-to-[CN2] | −0.75 ± 5.53 | [D1]-to-D2 | 9.21 ± 6.14 | 0.0000 | 0.0000 | Yes |
| 6 | CN1-to-[CN2] | −0.75 ± 5.53 | [nD2] | 12.33 ± 10.89 | 0.0000 | 0.0000 | Yes |
| 7 | [CN]-to-D1 | 3.10 ± 7.72 | D1-to-[CN] | 2.90 ± 7.19 | 0.9219 | 1.0000 | No |
| 8 | [CN]-to-D1 | 3.10 ± 7.72 | [D1]-to-CN | 2.99 ± 7.16 | 0.9555 | 1.0000 | No |
| 9 | [CN]-to-D1 | 3.10 ± 7.72 | [nD1] | 5.48 ± 6.68 | 0.1774 | 0.2192 | No |
| 10 | [CN]-to-D1 | 3.10 ± 7.72 | [D1]-to-D2 | 9.21 ± 6.14 | 0.0012 | 0.0028 | Yes |
| 11 | [CN]-to-D1 | 3.10 ± 7.72 | [nD2] | 12.33 ± 10.89 | 0.0004 | 0.0020 | Yes |
| 12 | D1-to-[CN] | 2.90 ± 7.19 | [D1]-to-CN | 2.99 ± 7.16 | 0.9663 | 0.9663 | No |
| 13 | D1-to-[CN] | 2.90 ± 7.19 | [nD1] | 5.48 ± 6.68 | 0.1610 | 0.2255 | No |
| 14 | D1-to-[CN] | 2.90 ± 7.19 | [D1]-to-D2 | 9.21 ± 6.14 | 0.0012 | 0.0035 | Yes |
| 15 | D1-to-[CN] | 2.90 ± 7.19 | [nD2] | 12.33 ± 10.89 | 0.0008 | 0.0028 | Yes |
| 16 | [D1]-to-CN | 2.99 ± 7.16 | [nD1] | 5.48 ± 6.68 | 0.1696 | 0.2227 | No |
| 17 | [D1]-to-CN | 2.99 ± 7.16 | [D1]-to-D2 | 9.21 ± 6.14 | 0.0012 | 0.0031 | Yes |
| 18 | [D1]-to-CN | 2.99 ± 7.16 | [nD2] | 12.33 ± 10.89 | 0.0007 | 0.0030 | Yes |
| 19 | [nD1] | 5.48 ± 6.68 | [D1]-to-D2 | 9.21 ± 6.14 | 0.0271 | 0.0406 | Yes |
| 20 | [nD1] | 5.48 ± 6.68 | [nD2] | 12.33 ± 10.89 | 0.0044 | 0.0093 | Yes |
| 21 | [D1]-to-D2 | 9.21 ± 6.14 | [nD2] | 12.33 + 10.89 | 0.2006 | 0.2340 | No |

CDR: Clinical Dementia Rating;
CN: CDR = 0 (Cognitively Normal);
D1: CDR = 0.5;
D2: CDR = 1;
PAD: Predicted Age Difference;
FDR: False Discovery Rate.

6. dMRI-Brain Age

Data in the CN-Modeling group were used to train the dMRI-brain age model. The Gaussian process regression method was used to regress the chronological age of the participants against the FA and MD values inside the WM region. After the training process, this model was applied to each MRI data in other groups to estimate the dMRI-brain age. The predicted age difference (PAD) was calculated by subtracting the chronological age from the dMRI-brain age. The performance of the model was tested in the CN1 group and quantified by the mean absolute error (MAE) and the Pearson's correlation coefficient (r) between the dMRI-brain age and chronological age.

7. Statistical Inference

PAD values were compared between any two of the seven groups, namely CN1-to-[CN2], [CN]-to-D1, D1-to-[CN],

[D1]-to-CN, [nD1], [D1]-to-D2, and [nD2]; amounting to 21 pairwise comparisons. For each pair of groups, two sample t-test was conducted. The Benjamini-Hochberg procedure with a false discovery rate (FDR) of 0.05 was used to determine if a test was considered statistically significant.

Results i. Comparison Between Different CDR Levels

Figure 10:
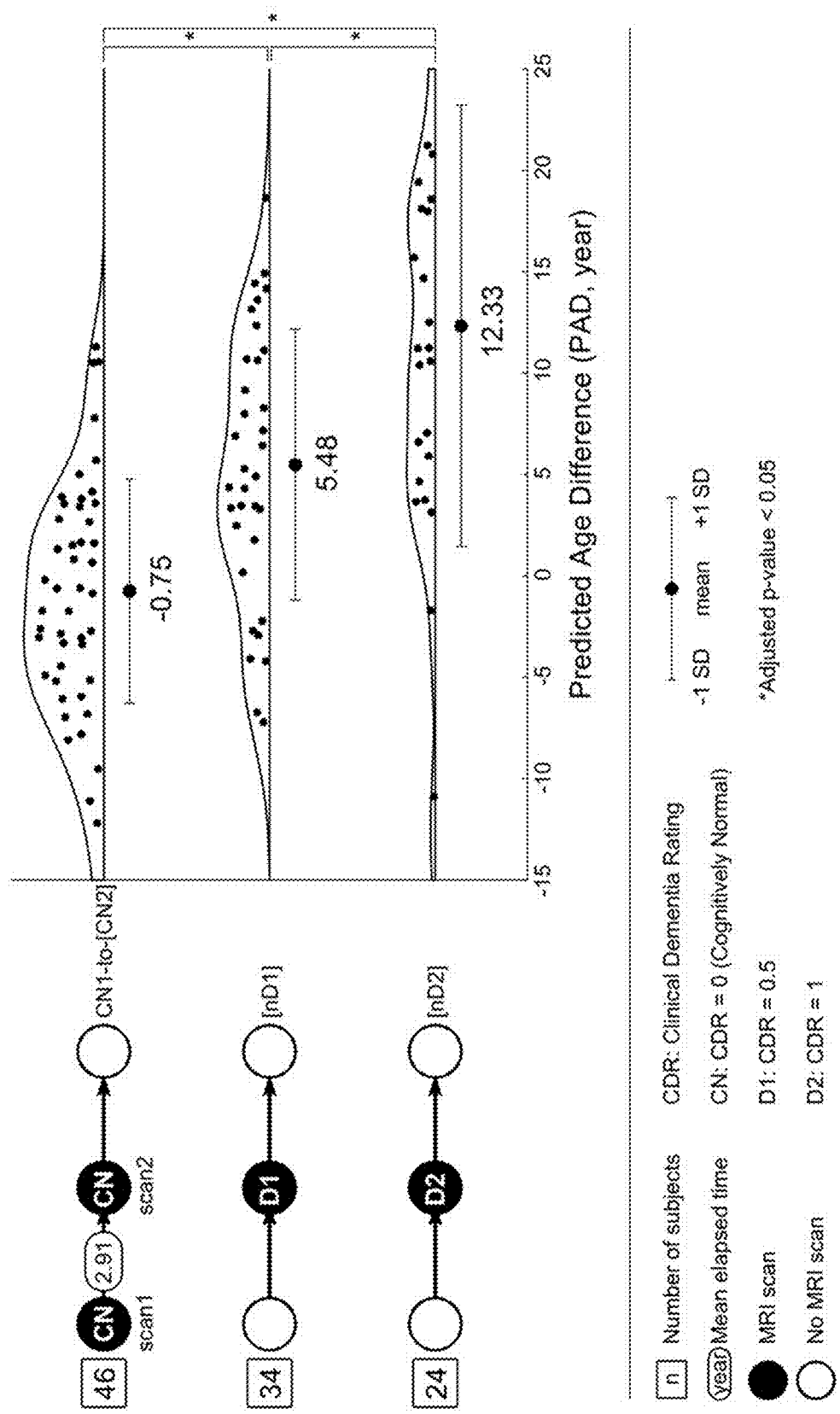
FIG. 10 shows comparisons between CN1-to-[CN2], [nD1], and [nD2] of Example 2.

FIG. 10 shows the groups with different CDR levels, i.e., CN1-to-[CN2], [nD1], and [nD2]. The mean and standard deviation of PAD values of CN1-to-[CN2], [nD1], and [nD2] were −0.75±5.53, 5.48±6.68, and 12.33±10.89 years, respectively. All comparisons on the three pairs of groups showed statistically significant differences (Table 2, #4, #6, #20). The results indicated that the higher the CDR level, the higher the PAD values.

ii. Comparison within Participants with Baseline CDR of 0.5

Figure 11:
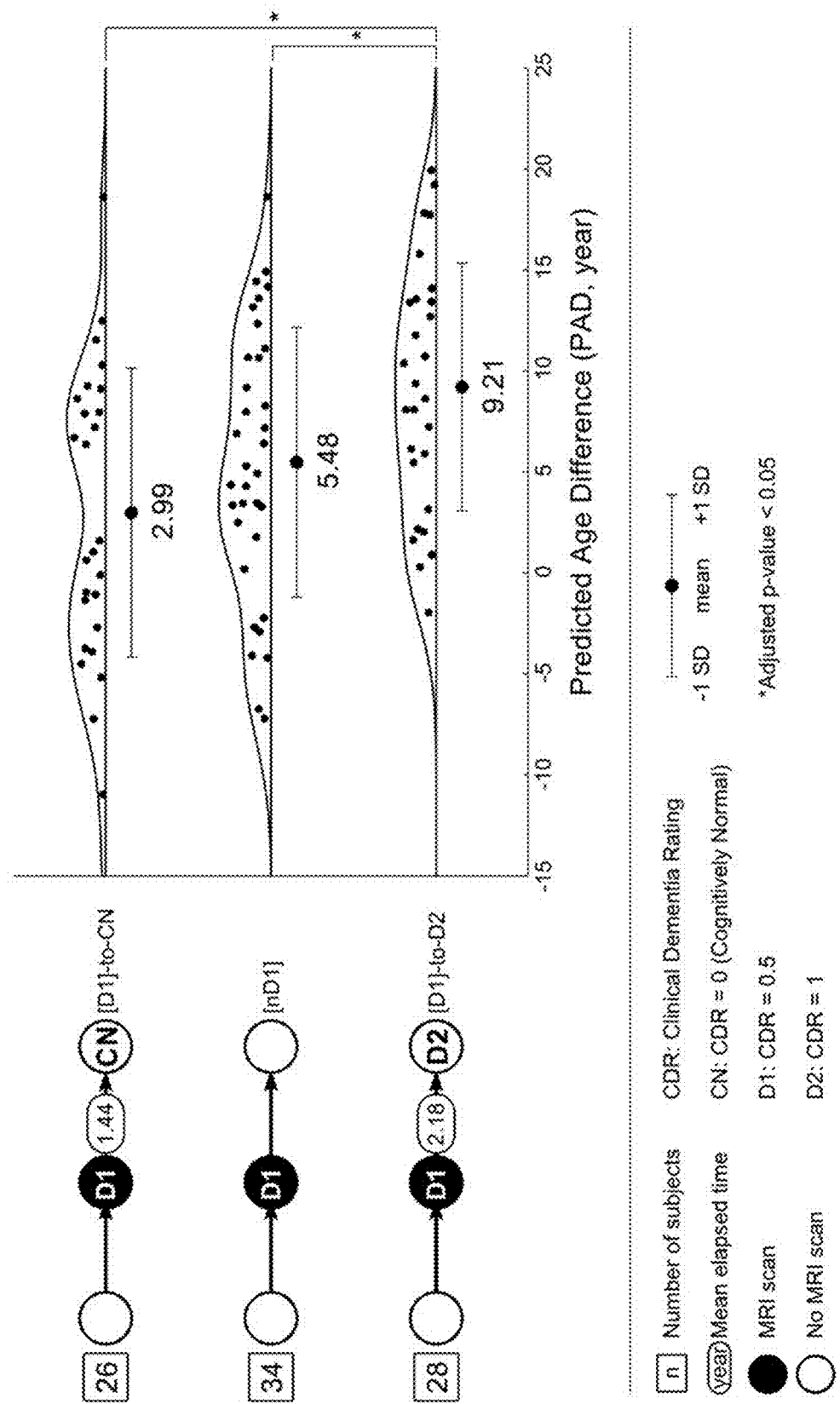
FIG. 11 shows comparisons between [D1]-to-CN, [nD1], and [D1]-to-D2 of Example 2.

FIG. 11 shows the participants who had the CDR of 0.5 at the time of MRI scanning who reverted to CN ([D1]-to-CN), stayed relatively stable ([nD1]), or converted to D2 ([D1]-to-D2) in 2 to 3 years (FIG. 11). The mean and standard deviation of PAD values of [D1]-to-CN, [nD1], and [D1]-to-D2 were 2.99±7.16, 5.48±6.68, 9.21±6.14 years, respectively. The PAD value in [D1]-to-D2 was significantly higher than that in [D1]-to-CN (adjusted p=0.0031) and that in [nD1] (adjusted p=0.0406) (Table 2, #17, #19). The PAD value in [D1]-to-CN was lower than that in [nD1], but the comparison between the two groups did not reach statistical significance (adjusted p=0.2227) (Table 2, #16).

iii. Comparison within Participants with Baseline CDR of 0

Figure 12:
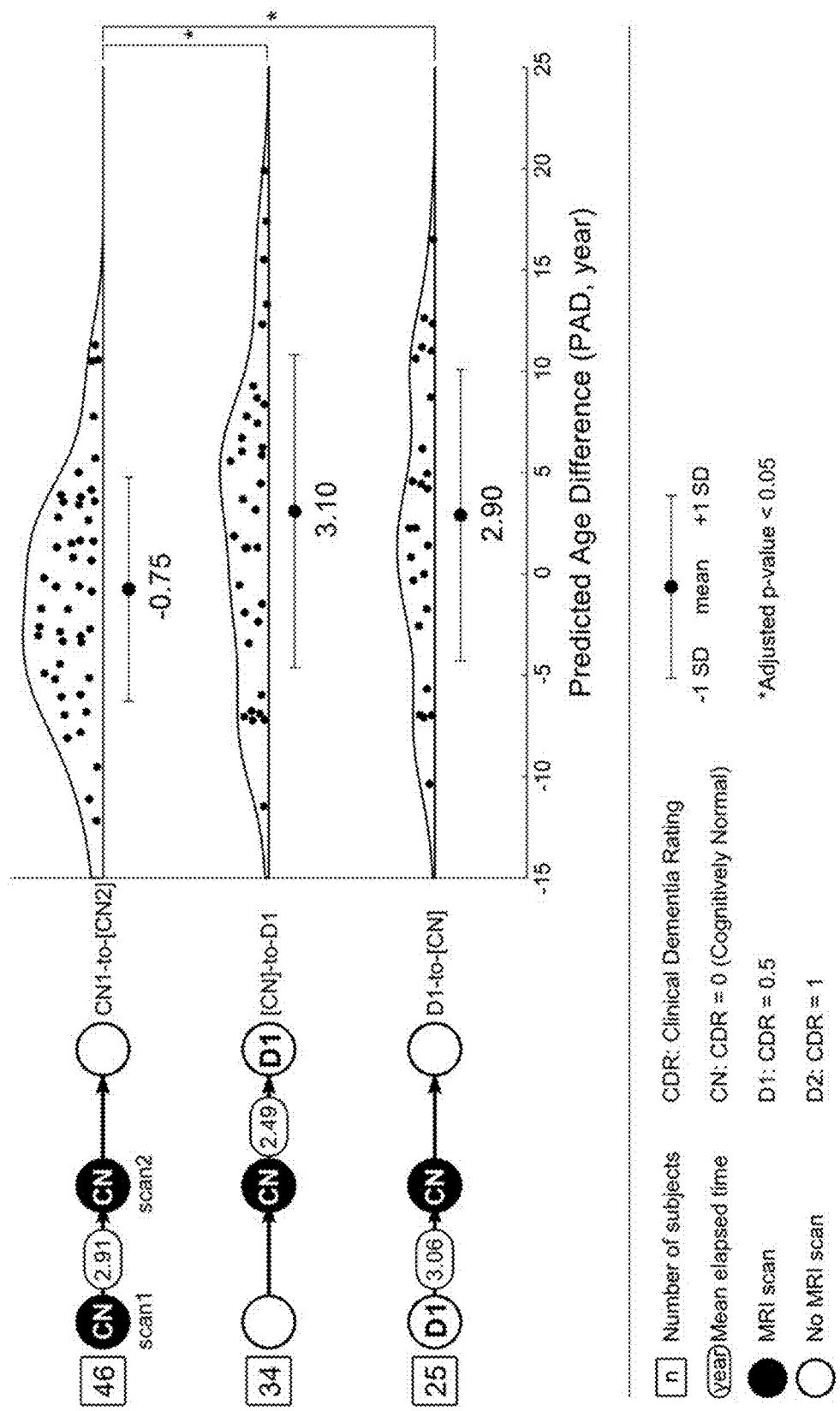
FIG. 12 shows comparisons between CN1-to-[CN2], D1-to-[CN], and [CN]-to-D1 of Example 2.

FIG. 12 shows the participants who were in CN at the time of MRI scanning but presented relatively stable (CN1-to-[CN2]) or unstable states ([CN]-to-D1 and D1-to-[CN]) in 1 to 2 years. The mean and standard deviation of PAD values of CN1-to-[CN2], [CN]-to-D1, and D1-to-[CN] were −0.75 5.53, 3.10±7.72, and 2.90±7.19 years, respectively. Both groups of [CN]-to-D1 (adjusted p=0.0213) and D1-to-[CN] (adjusted p=0.0318) had PAD values significantly higher than the CN1-to-[CN2] group (Table 2, #1, #2). There was no significant difference between the [CN]-to-D1 and D1-to-[CN] groups (adjusted p=1.0000) (Table 2, #7).

iv. Spectrum of PAD

Figure 13:
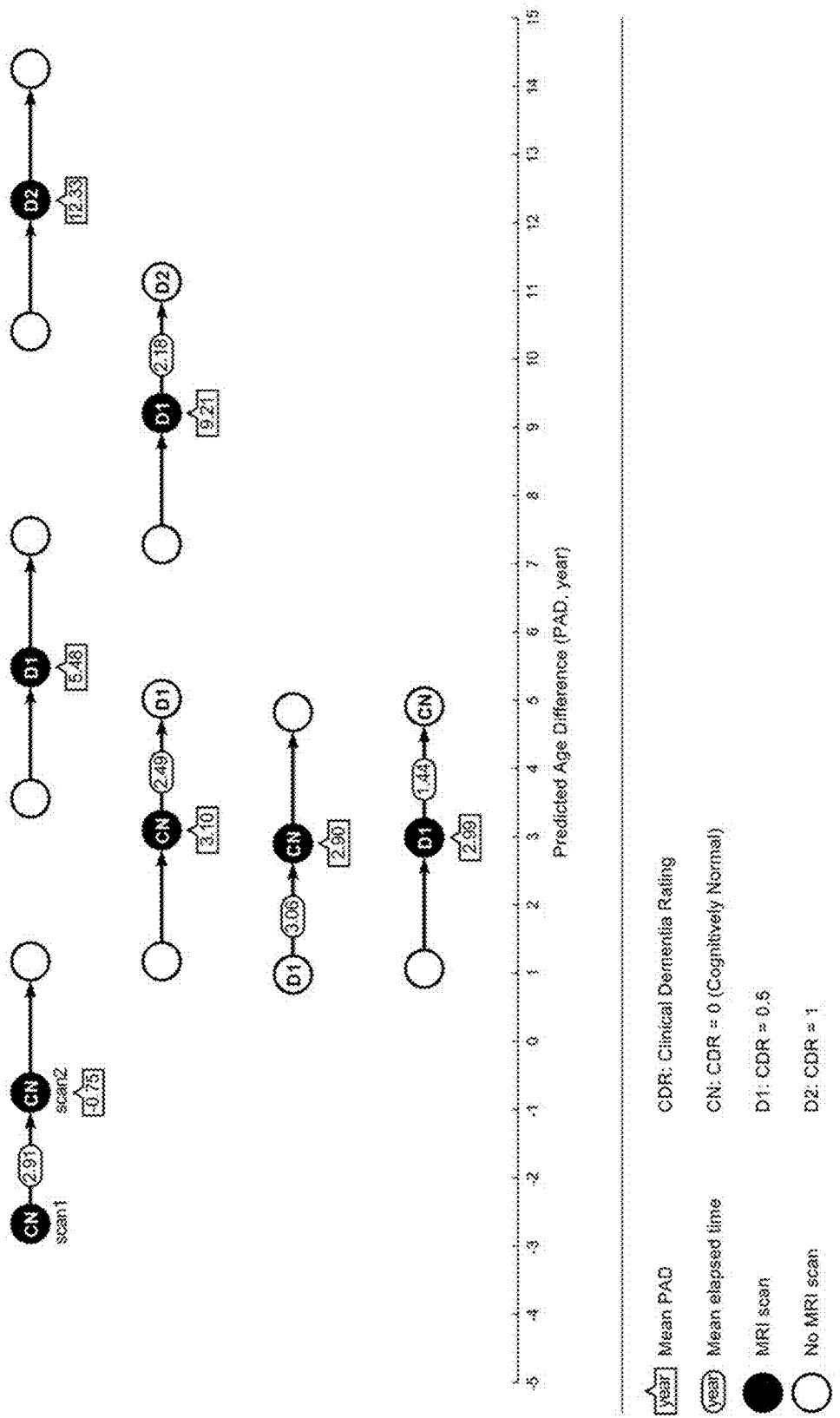
FIG. 13 shows spectrum of PAD.

FIG. 13 shows the seven groups sorted by their mean PAD values, and one can observe five sub-groups as follow. The first sub-group comprised the participants with relatively stable normal cognition (CN1-to-[CN2]), and the mean PAD of which was approximately 0 years. The second sub-group included those exhibiting transitions between CN and D1 (i.e. [CN]-to-D1, D1-to-[CN], and [D1]-to-CN), and the mean PADs were approximately 3 years. The third, fourth and fifth sub-groups were the participants with [nD1], [D1]-to-D2, and [nD2], with the mean PAD of 5.48, 9.21 and 12.33 years, respectively.

In conclusion, for older people with the CDR of 0, 0.5 and 1, DTI-derived PAD corresponds to the CDR scores, and PAD differs between people with relatively stable CDR and those with the CDR changed to higher scores in a couple of years. The results produced by the present invention suggest that PAD is essential in grading the dementia severity and predicting the change of severity in a few years. The capability of PAD can solve the current limitations of the CDR which is subjected to inaccurate information obtained from unreliable informants and inability to predict CDR change in the coming years. Therefore, the solution in the present invention can be a surrogate marker of the concomitant CDR and, furthermore, a prediction marker of the CDR change 2 to 3 years from the baseline.

Association of PAD with Low to Moderate Severity of Dementia

In the present invention, it is demonstrated that PAD derived from white matter microstructural property, as indicated by FA and MD of DTI, was associated with the CDR of 0, 0.5 and 1 (FIG. 10).

PAD in Patients with the Baseline CDR of 0.5 is Associated with the CDR Change in 1 to 2 Years In patients with the CDR of 0.5, they presented different outcomes in approximately 1 to 2 years (FIG. 11). The present invention demonstrated that PADs among these patients were significantly different. Patients whose CDR changed from 0.5 to 1 in approximately 2 years had mean PAD of 9.21 years, significantly higher than patients with constant CDR of 0.5 (mean PAD=5.48 years, adjusted p=0.0406) or those with the baseline CDR of 0.5 but turned to 0 in approximately 1.5 years (mean PAD=2.99 years, adjusted p=0.0031). The results have clinical implications. Currently exercise and cognitive training are the interventions recommended for patients with MCI (Petersen et al., 2018), whose CDR is mostly 0.5. However, no information is available to predict each patient's cognitive decline, and therefore, the intervention cannot be further tailored to each individual patient according to the decline risk. Findings in the present invention imply that PAD may be useful to stratify patients with MCI into high risk group (CDR changed from 0.5 to 1) and low risk group (constant CDR of 0.5 or CDR changed from 0.5 to 0). Appropriate intervention can then be designed for different risk groups.

PAD in Patients with Baseline CDR of 0 is Associated with the CDR Change in 2 to 3 Years The present invention also showed that participants with constant CDR of 0 had significantly different PAD from those with baseline CDR of 0 but turned to 0.5 in approximately 2.5 year (mean PAD: −0.75 years vs. 3.10 years, adjusted p=0.0213; FIG. 12). The results indicate that there is a variation of PAD even in cognitively normal people. Multiple brain age studies on cognitively normal people have demonstrated that PAD is associated with lifestyle factors, such as physical exercise, alcohol and tobacco consumption and interpersonal relationship, and cardiovascular risks, such as blood pressure, diabetes and body mass index (Cole, 2020; Hatton et al., 2018; Kolbeinsson et al., 2020; Ning et al., 2020; Ronan et al., 2016; Steffener et al., 2016). These studies suggest that, to some extent, the variation of PAD arises from health-related risk factors of each individual, the more the risk factors, the higher the PAD. Moreover, many epidemiological studies have shown that poor health-related risk factors have higher risks of afflicting dementia later in life (Akbaraly et al., 2019; Cations et al., 2016; Fayosse et al., 2020; Kivipelto et al., 2006; Mukadam et al., 2019; WHO, 2019). To sum, previous studies reported the association between PAD and lifestyle risk factors, and the associations between lifestyle factors and dementia. The present study further suggests that for the cognitively healthy people above 60 years old (approximately mean−SD=69.10-7.86 years in Table 1, CN1-to-[CN2]), those with PAD higher than 10 years (approximately mean+SD=3.10+7.72 years in Table 2, [CN]-to-D1) might be more likely to become cognitively impaired (CDR=0.5) in 3 years than those with PAD lower than −6 years (approximately mean−SD=−0.75-5.53 years in Table 2, CN1-to-[CN2]).

Correspondence of PAD with Stable and Meta-Stable CDR States

The present invention found that some of the groups in the study population exhibited relatively stable CDR scores in 2 to 3 years, i.e., CN1-to-[CN2], [nD1] and [nD2], while some groups presented relatively rapid transitions of the CDR, i.e., [CN]-to-D1, D1-to-[CN], [D1]-to-CN, and [D1]-to-D2 (Table 2). Notably, when labeling each group with PAD, a continuum of PAD revealed across the relatively stable and meta-stable groups (FIG. 13). PAD was smallest in the cognitively normal group (CN, −0.75 years), followed by 3 meta-stable groups ([CN]-to-D1, D1-to-[CN], and [D1]-to-CN, presenting 3.10, 2.90, and 2.99 years, respectively), the relatively stable group of CDR=0.5 ([nD1], 5.48 years), another meta-stable group ([D1]-to-D2, 9.21 years), and the largest in the relatively stable group of CDR=1 or beyond ([nD2], 12.33 years). The spectrum of PAD corresponding to the stable and meta-stable states of the CDR provides a new perspective to the CDR in elderly people. Given a CDR score of 0, 0.5, or 1 of an individual, one could use PAD to predict the probability of staying cognitively normal (CDR=0) or transitioning to a different CDR stage (CDR=0.5 or 1) in a couple of years.

Example 3

Another example of the current invention provides proof of concept to support the proposed intended use of the device. The computer based program reads the specified brain image data of an individual as inputs and estimates the person's PAD, and according to the predefined cutoff value of PAD, the program determines whether the person is likely/or unlikely to be cognitively normal if he/she were assessed by the CDR.

A retrospective study on a cohort of a databank OASIS-3 was performed with the current invention, which evaluated the performance of PAD in identifying patients who were likely/or unlikely to be cognitively normal (CDR=0) by comparing the results with patient's CDR scores.

To obtain positive predictive value (PPV), negative predictive value (NPV), sensitivity, specificity, odds ratio (OR), and accuracy of distinguishing between CDR>0 and CDR=0 at different cutoff values of PAD.

Data Selection

Same to Example 3, participants in OASIS-3 of Example 3 undertook one to multiple sessions of brain MRI scanning on three 3T MRI scanners (Siemens, Erlangen, Germany) including two scanner models, i.e., Biograph and TIM Trio. To reduce scanner-wise variability, MRI data acquired from the same scanner model (TIM Trio) using the same acquisition scheme for T1-weighted (T1w) imaging and diffusion tensor imaging (DTI) were selected for the analysis. Since the analysis required acceptable image quality of T1w and DTI data, participants whose images presented severe image artefact such as motion blurring on T1w or failed artefact correction on DTI were excluded. A total of 529 participants in 575 MRI scanning sessions were enrolled for subsequent analysis met the selection criteria.

Grouping According to the CDR

The participants enrolled in the study were grouped into 5 groups according to the track records of their CDR values. The 5 groups were named as follow: [CN]-Modeling, [CN1]-to-CN2, CN1-to-[CN2], [nD1], and [nD2]. All groups were mutually exclusive except [CN1]-to-CN2 and CN1-to-[CN2] which recruited the same participants, undertaking the first and second MRI scanning, respectively. The characteristics of the 5 groups were described below.

i) [CN]-Modeling: This group comprised 258 participants who were cognitively normal (CDR=0, CN for short) and stable. The CDR was 0 in all clinical records and had at least one such record within 1 year before or after the MRI scanning. The data in this group served as the training data to build the dMRI-brain age model. [CN] denotes the cognitive status of CN around the time of MR scanning.

ii) [CN1]-to-CN2: This group comprised 46 participants who were cognitively normal and stable. The screening criteria were the same as the [CN]-Modeling group. The data in this group served as the testing data of the dMRI-brain age modeling. [CN1] denotes that the participants were CN around the time of the first MR scanning.

iii) CN1-to-[CN2]: Participants in this group (N=46) were the same participants as those in [CN1]-to-CN2. As described above, the MRI scanning date in this group was later than that in [CN1]-to-CN2 with the inter-scan interval of 2.91±0.67 years. [CN2] denotes that the participants were CN around the time of the second MR scanning.

iv) [nD1]: Participants in this group (N=34) were in D1 within the interval of 180 days from the MRI scanning date. After the interval, 19 participants had at least one clinical record showing that they stayed in the D1 stage, while rest of the participants (N=15) did not have any record of the CDR available. Therefore, nominal D1 (nD1 for short) was named for this group. [nD1] denotes that the participants were in nominal D1 around the time of MRI scanning.

v) [nD2]: Participants in this group (N=24) were in D2 within the interval of 180 days from the MRI scanning date. After the interval, 13 participants converted to moderate symptomatic AD (CDR=2, D3 for short), 6 participants had at least one clinical record showing that they stayed unchanged, and 5 participants did not have any CDR record. Therefore, nominal D2 (nD2 for short) was named for this group. [nD2] denotes that the participants were in nominal D2 around the time of MRI scanning.

Analysis and Statistics

Brain age modeling: Data in the [CN]-Modeling group were used to train the dMRI-brain age model. The Gaussian Process Regression method was used to regress the chronological age of the participants against the DTI indices of the brain. After the training process, the model was applied to each MRI data in other groups to estimate the dMRI-brain age. The predicted age difference (PAD) was calculated by subtracting the chronological age from the dMRI-brain age. The performance of the model was tested in the [CN1]-to-CN2 group and quantified by the mean absolute error (MAE) and the Pearson's correlation coefficient (r) between the dMRI-brain age and chronological age.

Group comparison: PAD values were compared between any two of the three groups, namely CN1-to-[CN2], [nD1], and [nD2], amounting to 3 pairwise comparisons. For each pair of groups, two sample t-test was conducted. The Benjamini-Hochberg procedure with a false discovery rate (FDR) of 0.05 was used to determine if a test was considered statistically significant.

Performance of the intended use: To evaluate the performance of PAD in ruling out cognitively normal condition, the present invention pooled the [nD1] and [nD2] groups to form a new group (named [nD1]+[nD2]) to represent the group with CDR>0 which is to be ruled out by our intended use. The receiver operating characteristic (ROC) curve analysis was performed to evaluate the accuracy of PAD in differentiating between CDR=0 and CDR>0. Positive predictive value (PPV), negative predictive value (NPV), sensitivity, specificity, and odds ratio (OR) of differentiating between CDR>0 and CDR=0 was evaluated at different cutoff values of PAD.

Results

Demographics: Table 3 summarizes the demographics of the 5 groups including [CN]-Modeling (training data), [CN1]-to-CN2 (testing data) and 3 comparison groups, namely CN1-to-[CN2], [nD1], and [nD2]. Qualitatively, it can be seen a tendency of the increase in the CDR and PAD and the decrease in the MMSE from CN1-to-[CN2], [nD1] to [nD2].

TABLE 3

Demographics

| Group | Category | Elapsed Time (years) | Sample Size | Gender Female | Age Male | MMSE (years) | CDR | Education (sum of box) | APOE e4‡ (years) | PAD | (years) |
|---|---|---|---|---|---|---|---|---|---|---|---|
| [CN]-Modeling | Training Data | | 258 | 57.80% | 42.20% | 68.54 ± 8.75 | 29.24 ± 1.17 | 0.01 ± 0.06 | 16.22 ± 2.47 | 31.90% | |
| [CN1]-to-CN2 | Testing Data | 2.91 ± 0.67† | 46 | 65.20% | 34.80% | 66.19 ± 8.13 | 29.17 ± 0.93 | 0.00 ± 0.00 | 16.13 ± 2.60 | 34.80% | −0.86 ± 5.48 |
| CN1-to-[CN2] | Statistical Analysis | 2.91 ± 0.67† | 46 | 65.20% | 34.80% | 69.10 ± 7.86 | 29.09 ± 1.15 | 0.00 ± 0.00 | 16.13 ± 2.60 | 34.80% | −0.75 ± 5.53 |
| [nD1] | Statistical Analysis | | 34 | 50.00% | 50.00% | 76.23 ± 7.21 | 26.65 ± 2.91 | 1.91 ± 0.97 | 14.91 ± 3.39 | 52.90% | 5.48 ± 6.68 |
| [nD2] | Statistical Analysis | | 24 | 33.30% | 66.70% | 76.40 ± 10.31 | 21.13 ± 3.89 | 5.46 ± 1.11 | 13.71 ± 2.93 | 54.20% | 12.33 ± 10.89 |

MMSE: Mini-Mental State Examination;
CDR: Clinical Dementia Rating;
CN: CDR = 0 (Cognitively Normal);
D1: CDR = 0.5;
D2: CDR = 1;
PAD: Predicted Age Difference,
†The elapsed time here represents the inter-scan interval between [CN1]-to-CN2 and CN1-to-[CN2].
‡APOE e4 means the percentage in the group population that poses either one or two e4 alleles.

Performance of brain age prediction: The model performance tested in the [CN1]-to-CN2 group (testing data) gave MAE=4.35±3.39 years and r=0.77 (p-value=3.64×10$^{-10}$)

Figure 21:
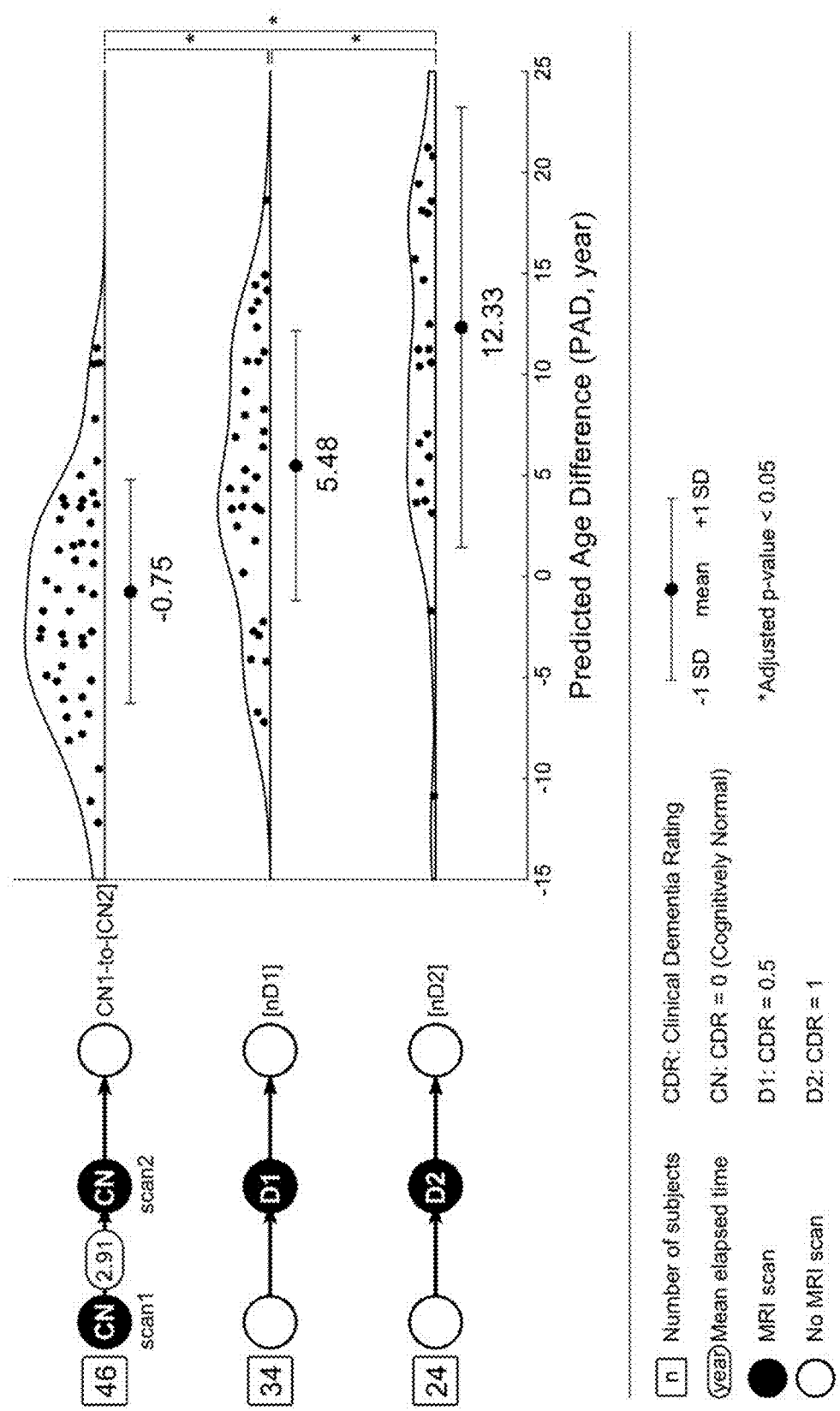
FIG. 21 shows the PAD comparisons between CN1-to-[CN2], [nD1], and [nD2] of Example 3.

Group comparison: FIG. 21 shows the groups with different CDR levels, i.e., CN1-to-[CN2], [nD1], and [nD2]. The mean and standard deviation of PAD values of CN1-to-[CN2], [nD1], and [nD2] were −0.75±5.53, 5.48±6.68, and 12.33±10.89 years, respectively. All comparisons on the three pairs of groups showed statistically significant differences. The results indicated that the higher the CDR level, the higher the PAD values.

Figure 22:
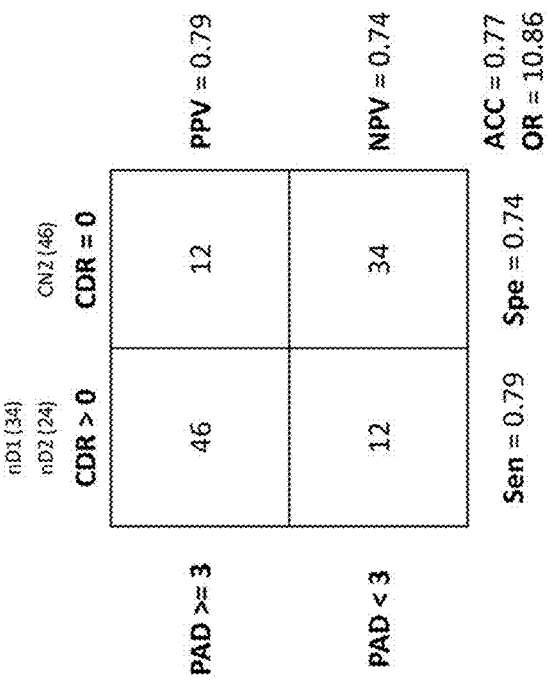
FIG. 22 shows the ROC curve analysis to evaluate the performance of differentiating between CDR=0 and CDR>0.
Figure 22:
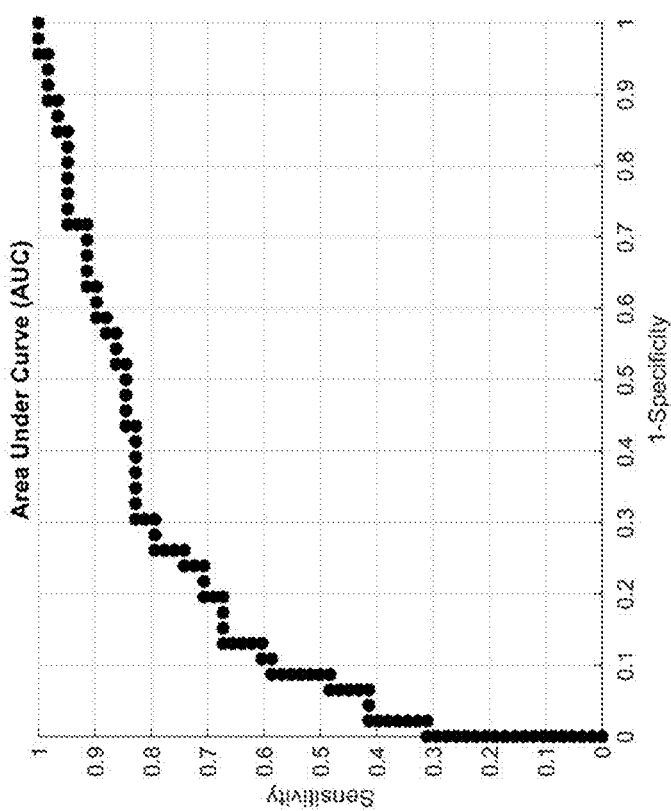

ROC curve analysis: FIG. 22 shows the results of the ROC curve analysis. Area under the curve (AUC) was 0.82.

Table 4 lists the performance of differentiating between CDR=0 and CDR>0 at different cutoff values of PAD. The best cutoff value of PAD was found to be 3 years. Using PAD=3 as the cutoff value, the performance of differentiating between CDR=0 and CDR>0 showed sensitivity=0.79, specificity=0.74, PPV=0.79, NPV=0.74, OR=10.86, and accuracy=0.77.

In FIG. 22, ROC curve analysis to evaluate the performance of differentiating between CDR=0 and CDR>0. Abbreviation: PAD=predicted age difference, CDR=clinical dementia rating, Sen=sensitivity, Spe=specificity, PPV=positive predicted value, NPV=negative predicted value, ACC=accuracy, OR=odds ratio.

TABLE 4

The performance of differentiating between CDR = 0 and CDR > 0 at different cutoff values of PAD.

| PAD | TP | FP | FN | TN | OR | ACC | PPV | NPV | Sens. | Spec. | AUC |
|---|---|---|---|---|---|---|---|---|---|---|---|
| 0 | 43 | 20 | 9 | 26 | 7.08 | 0.72 | 0.71 | 0.74 | 0.84 | 0.57 | 0.82 |
| 1 | 48 | 18 | 10 | 28 | 7.47 | 0.73 | 0.73 | 0.74 | 0.83 | 0.61 | |
| 2 | 47 | 14 | 11 | 32 | 9.77 | 0.76 | 0.77 | 0.74 | 0.81 | 0.70 | |
| 3 | 46 | 12 | 12 | 34 | 10.86 | 0.77 | 0.79 | 0.74 | 0.79 | 0.74 | |
| 4 | 39 | 7 | 19 | 39 | 11.44 | 0.75 | 0.85 | 0.67 | 0.67 | 0.85 | |
| 5 | 35 | 6 | 23 | 40 | 10.14 | 0.72 | 0.85 | 0.63 | 0.60 | 0.87 | |
| 6 | 33 | 4 | 25 | 42 | 13.86 | 0.72 | 0.89 | 0.63 | 0.57 | 0.91 | |
| 7 | 30 | 4 | 28 | 42 | 11.25 | 0.69 | 0.88 | 0.60 | 0.52 | 0.91 | |
| 8 | 27 | 3 | 31 | 43 | 12.48 | 0.67 | 0.90 | 0.58 | 0.47 | 0.93 | |
| 9 | 26 | 3 | 32 | 43 | 11.65 | 0.66 | 0.90 | 0.57 | 0.45 | 0.93 | |
| 10 | 25 | 3 | 33 | 43 | 10.86 | 0.65 | 0.89 | 0.57 | 0.43 | 0.93 | |

Abbreviation:
PAD = predicted age difference,
TP = true positive,
FP = false positive,
FN = false negative,
TN = true negative,
OR = odds ratio,
ACC = accuracy,
PPV = positive predictive value,
NPV = negative predictive value,
Sens. = sensitivity,
Spec. = specificity,
AUC = area under the curve.

Conclusion

Figure 23:
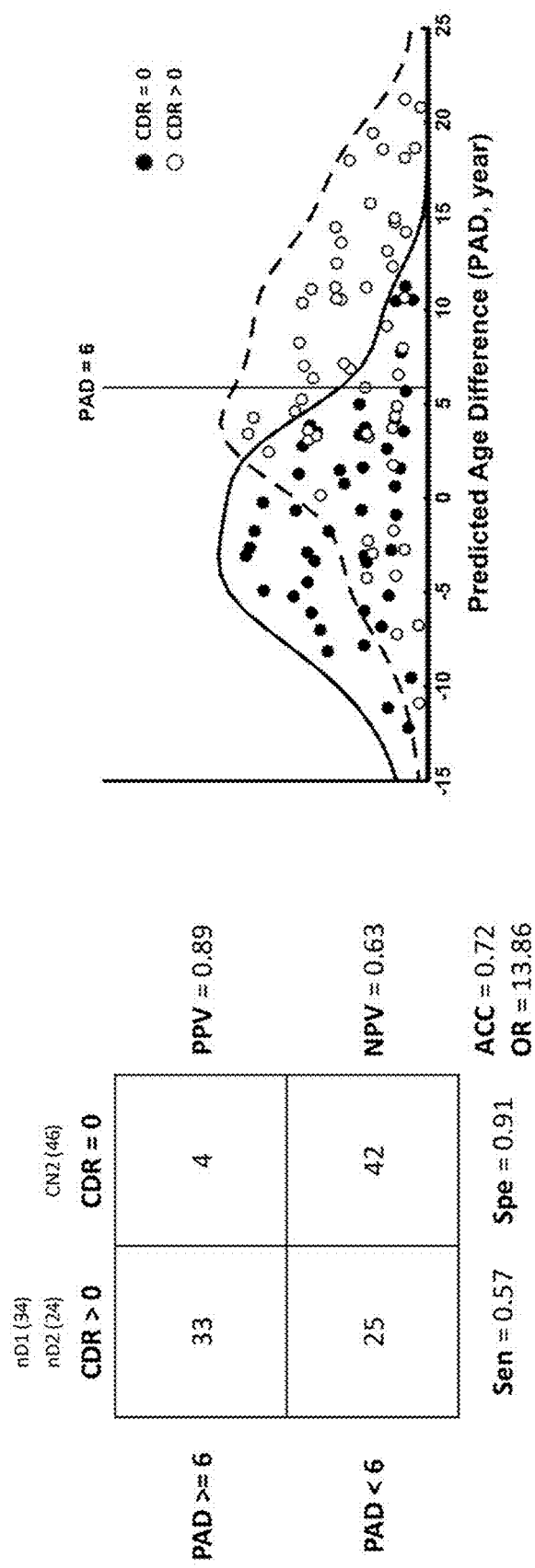
FIG. 23 shows the confusion matrix of the results using the cutoff PAD of 6, and the distribution of the two populations (i.e. CDR=0 and CDR>0) with respect to PAD.

The current invention shows that the best cutoff value of PAD for differentiating between CDR=0 and CDR>0 is 3 years, resulting in sensitivity=0.79, specificity=0.74, PPV=0.79, NPV=0.74, OR=10.86, and accuracy=0.77. However, the intended use is to rule out CDR=0 in patients who are suspected to have dementia. With this intended use, the performance of PPV, specificity and OR, rather than sensitivity and accuracy, become the end points of primary interest. In this case, PAD=6 years appears to be the best cutoff value, giving PPV=0.89, specificity=0.91, and OR=13.86. FIG. 23 shows the confusion matrix of the results using the cutoff PAD of 6, and the distribution of the two populations (i.e. CDR=0 and CDR>0) with respect to PAD. The results mean that for those whose PAD>=6 years, 89% of them are not cognitively normal (i.e. CDR>0), and for those who are cognitively normal (i.e. CDR=0), 91% of them have PAD<6 years. The OR of 13.86, defined as (TP×TN)/(FP×FN), means the ratio of the true outcome (TP and TN) with respect to the false outcome (FP and FN) is more than 10 folds. On the other hand, using PAD=6 years as the cutoff value, sensitivity=0.57 and NPV=0.63. The results mean that for those who are not cognitively normal (i.e. CDR>0), 57% of them have PAD>=6 years, and for those who have PAD<6 years, 63% are cognitively normal (i.e. CDR=0). In sum, using PAD=6 years as the cutoff value has satisfactory performance to identify patients who are very unlikely to be cognitively normal, but it performs poorly in identifying those who are cognitively normal. Therefore, we conclude that the satisfactory performance of PPV and OR supports the intended use of our proposed device.

Importantly, it should be noted that the present invention is pioneering in the field of CDR estimation and prediction with respect to at least three aspects. First, the brain age model being built by the present invention is based on the white matter microstructural metrics, named dMRI-brain age and the resulting WM PAD. Second, what WM PAD does is to predict a person's concomitant measures of the CDR. Third, in addition, WM PAD also predicts the same person's CDR change 2 to 3 years from the time when dMRI-brain age is measured.

In contrast to the present invention, the existing method for estimating the CDR either built the brain age model on the basis of morphometric features of gray matter obtained from T1M MRI, named GM brain age and the resulting GM PAD, and found associations between GM PAD and concomitant measures of the CDR (Beheshti et al., 2018); or calculated FW content from diffusion MRI and found that FW was associated with concomitant measures of the CDR and future status of the CDR (Maillard et al., 2019).

Other researches and inventions in the field scrutinize the associations between MRI metrics and the whole array of cognitive performance measured by validated tools. In those results, it is reported that a particular MRI metric which is associated with a particular cognitive measure. However, the present invention establishes the unique correspondence between WM PAD and concomitant CDR, and the correspondence between WM PAD and CDR change 2 to 3 years later from the baseline. Such specific correspondence between dMRI-brain age and the CDR is not reported before and so it is not obvious to contemporary inventors.

WM PAD has the advantages over prior solutions due to (1) better sensitivity to the CDR than GM brain age, and (2) less susceptibility to the cerebrospinal fluid (CSF) partial volume effect than the FW metric.

First, WM PAD is more sensitive than GM brain age in distinguishing CDR scores. In the paper of Beheshti et al., they only showed the correlation between GM brain age and the CDR scores (from 0, 0.5 to 1). They did not show the results of comparison between brain age and the CDR, probably due to null results owing to marked overlaps between CDR scores (FIG. 7b in Beheshti's paper).

On the other hand, dMRI-brain age maybe less susceptible to the CSF partial volume effect induced by brain atrophy than is FW metric. Hypothetically, FW content is mainly attributed by the CSF partial volume effect in white matter neighboring the ventricles or cerebral sulci. The FW content would be likely to increase as the brain becomes atrophic with age. In other words, FW content is confounded by brain atrophy. By contrast, WM PAD is derived from FA and MD in the whole brain white matter. Although FA and MD values are likely to be altered in the white matter pixels adjacent to the ventricles and cerebral sulci, the effect is negligible because the number of pixels with the partial volume effect is substantially small as compared with the whole brain white matter pixels.

Example 4

The present invention discloses that gray matter brain age serves as a potential biomarker to predict cognitive outcomes in patients with MCI after 2 years of ChEI treatment, and can be used to aid the development of other novel therapeutics in MCI.

Methods and Materials

Data Source:

The study was a retrospective study using existing data in Taipei Medical School-Shuang Ho Hospital, New Taipei City, Taiwan. Patient data were retrieved from the ChEI treatment database and normal data were retrieved from the health check-up database. To build a gray matter brain age model, MRI data with normal cognition in the health check-up dataset were pooled together with MRI data of cognitively normal subjects in the OASIS-3 databank. The study was approved by the Institutional Review Board of Shuang Ho Hospital, New Taipei City, Taiwan.

Criteria for Eligible Data:

Patient data retrieved from the ChEI treatment database fulfilled the criteria as follow. (1) Age ranged from 50 to 85 years. (2) The ChEI treatment lasted for at least 2 years. (3) Cognitive evaluation including Mini-Mental State Evaluation (MMSE) and CDR was given at least twice. The first must be given upon entry of ChEI treatment, and another must be performed at least 2 years from the first. (4) There was no contradictory outcomes between CDR and MMSE. (5) MRI was performed within 120 days of the first cognitive evaluation. (6) Patients had no history of substance abuse, head trauma, neurological, psychiatric or metabolic disease.

According to the cognitive evaluation at two time points, patient data were divided into 2 groups, ChEI+ and ChEI−. Subjects in the ChEI+ group were those who were diagnosed as MCI at baseline and showed improvement or stable performance on either MMSE or CDR relative to the first evaluation. Subjects in the ChEI− group were those who were diagnosed as MCI at baseline and showed worsening on either MMSE or CDR of the second evaluation than the first. Any data with contradictory change between MMSE and CDR, i.e. improved in one metric and worsened in another or vice versa, was discarded.

Normal data retrieved from the health check-up database fulfilled the following criteria: (1) age 50 to 85 years old upon scanning, and (2) cognitively normal without history of substance abuse, head trauma, neurological, psychiatric or metabolic disease.

MRI Acquisition Sequences:

MRI data in Shuang Ho Hospital were acquired on three MRI systems (GE HealthCare, Chicago, Illinois, U.S.), two 1.5-Tesla scanners (Signa HDxt and Optima MR360) and one 3-Tesla scanners (Discovery MR750). Images were acquired using a routine clinical protocol including T1-weighted Fluid Attenuated Inversion Recovery (T1 FLAIR), T2-weighted FLAIR (T2 FLAIR) and T2-weighted Fast Recovery Fast Spin Echo (T2 FRFSE) pulse sequences. The matrix size used 512 and slice thickness used 7 mm uniformly across the three pulse sequences and three MRI systems. Other imaging parameters such as repetition time (TR), echo time (TE), inversion time (TI) and field of view (FOV) varied individually to optimize the scanning time. The T1 FLAIR sequence used the imaging parameters as follow: imaging plane=axial, TR=1786-3017 ms, TE=7.82-26.81 ms, TI=738-1058 ms, field-of-view (FOV)=220-250 mm. For the T2 FLAIR sequence, the imaging parameters were: imaging plane=axial, TR=8000-9000 ms, TE=117-148 ms, TI=2000-2470 ms, FOV=230-250 mm. For the T2 FRFSE sequence, the parameters were: imaging plane=coronal, TR=3626-6773 ms, effective TE=96-158 ms, FOV=220-250 mm.

T1-weighted MRI data retrieved from OASIS-3 were acquired from 3 scanners (Siemens, Erlangen, Germany), one 3-Tesla Biograph mMR PET/MR scanner and two 3-Tesla TIM Trio scanner. The imaging pulse sequence used the 3-dimensional magnetization prepared rapid gradient echo sequence (T1 MPRAGE). The imaging parameters were: TR=2,400 ms, TE=3.16 ms, TI=1,000 ms, FOV=256 mm×256 mm×176 mm, and matrix size=256×256×176.

Gray Matter Brain Age Model Building:

T1 FLAIR data from the Shuan Ho health check-up database and T1 MPRAGE data from cognitively normal subjects in OASIS-3 were pooled to build a gray matter brain age model. The resulting brain age model was then applied to T1 FLAIR data of patients in the Shuan Ho ChEI treatment database to calculate PAD for each patient.

Figure 26:
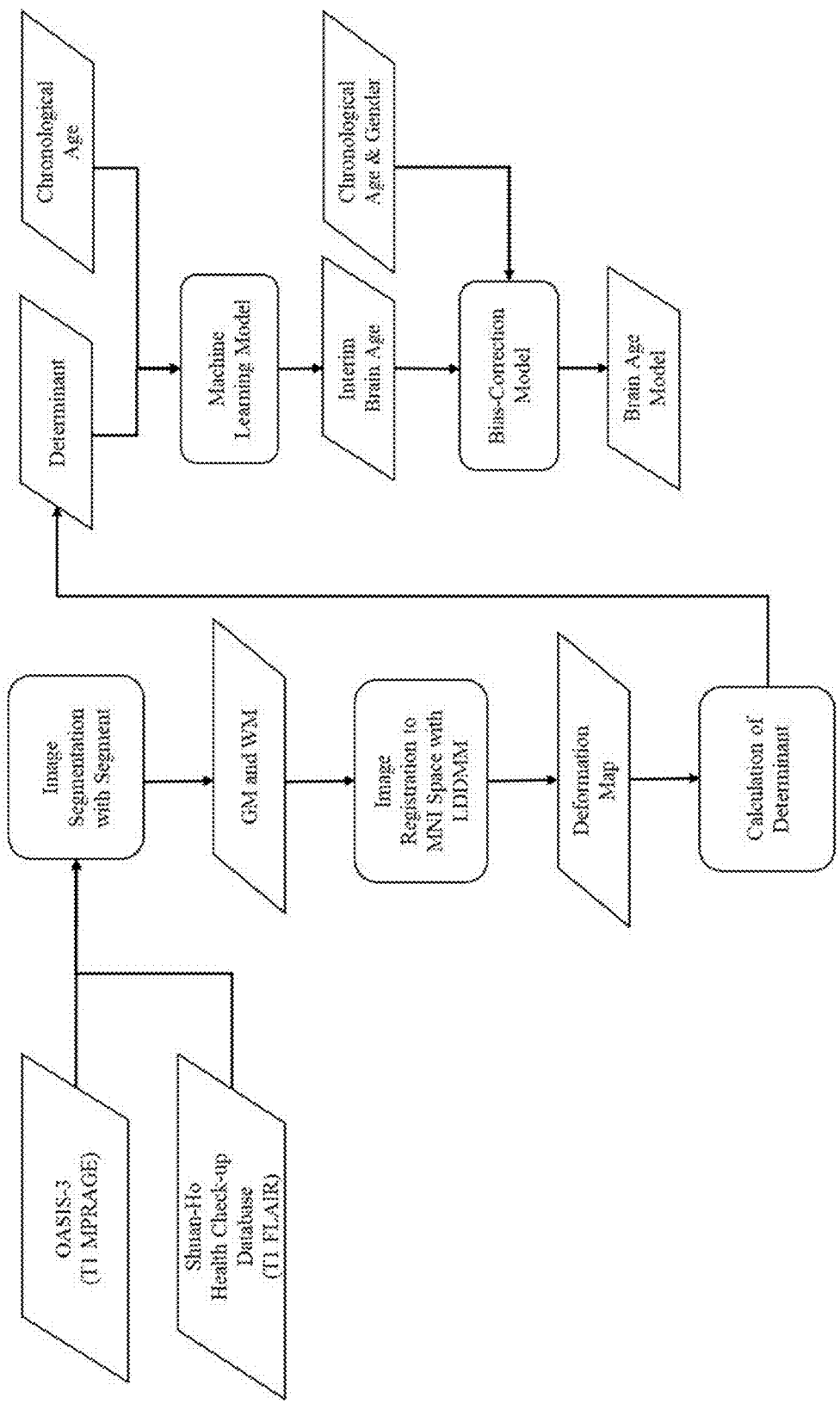
FIG. 26 shows a flow chart of gray matter brain age model building of Example 4.

Gray matter brain age model building underwent two major steps, data preprocessing and model construction, as shown in FIG. 26. Data preprocessing was performed on each healthy participant's T1-weighted images (T1 FLAIR or T1 MPRAGE) to extract gray matter features as inputs to the training algorithm. Gray matter and white matter were segmented from the T1-weighted images using the Segment toolbox of SPM12. The deformation map was then obtained by registering segmented gray matter and white matter images to a standard space established by the Montreal Neurological Institute (MNI Space). The image registration was conducted by in-house code using Large Deformation Diffeomorphic Metric Mapping (LDDMM), a generalized 3D nonlinear registration algorithm. The present invention then used the Jacobian determinants of the deformation in the gray matter region as the model features because the determinants indicated the ratio of local volume change compared to the reference frame in the MNI Space, inferring relative change of volume atrophy.

The determinants of gray matter and chronological age of each participant in the training dataset were used as the inputs to a machine learning algorithm. The present invention used Gaussian Process Regression (GPR) to construct the gray matter brain age model. Furthermore, in order to mitigate the age-related and sex-related bias, the present invention used the leave-one-out approach to construct the bias-correction model.

To test the performance of the model, the mean of the absolute difference between predicted brain age and chronological age (mean absolute error, MAE) and Pearson's correlation coefficient were adopted as test metrics. Since the model was to be applied to patient data which were acquired by the same 3 MRI scanners as the health check-up data, the test was performed on the same training data of Shuan Ho health check-up database using the leave-one-out technique.

Data Analysis:

The resulting gray matter brain age model was applied to T1 FLAIR of each individual patient to calculate brain age, and PAD was calculated by subtracting chronological age from predicted brain age.

To ensure balance of the potential covariates of ChEI response, demographic data of ChEI+ and ChEI− groups were recorded and compared. The demographic data included age, sex, education level, MMSE at baseline, ChEI agent type and dose, treatment duration, and living condition. In addition, two imaging biomarkers, Fazekas scale and medial temporal atrophy (MTA) score, were evaluated on T2 FLAIR and T2 FRFSE, respectively. Fazekas scale ranged from 0 to 3 indicating the severity of white matter hyperintensity, and MTA score ranged from 0 to 4 indicting the severity of hippocampal atrophy.

Statistics:

Demographic data were compared using two-sample t-test if the item belonged to continuous variable, and using Chi-square test if the item belonged to categorical variable.

Normal distribution of PAD in the two patient groups was tested by Shapiro Wilk Test and variance equality was checked by Levene Test. Two-sample t-test was then performed to test the difference in PAD between ChEI+ and ChEI− groups, and statistically significance was considered if p-value <0.05.

Results

Figure 27:
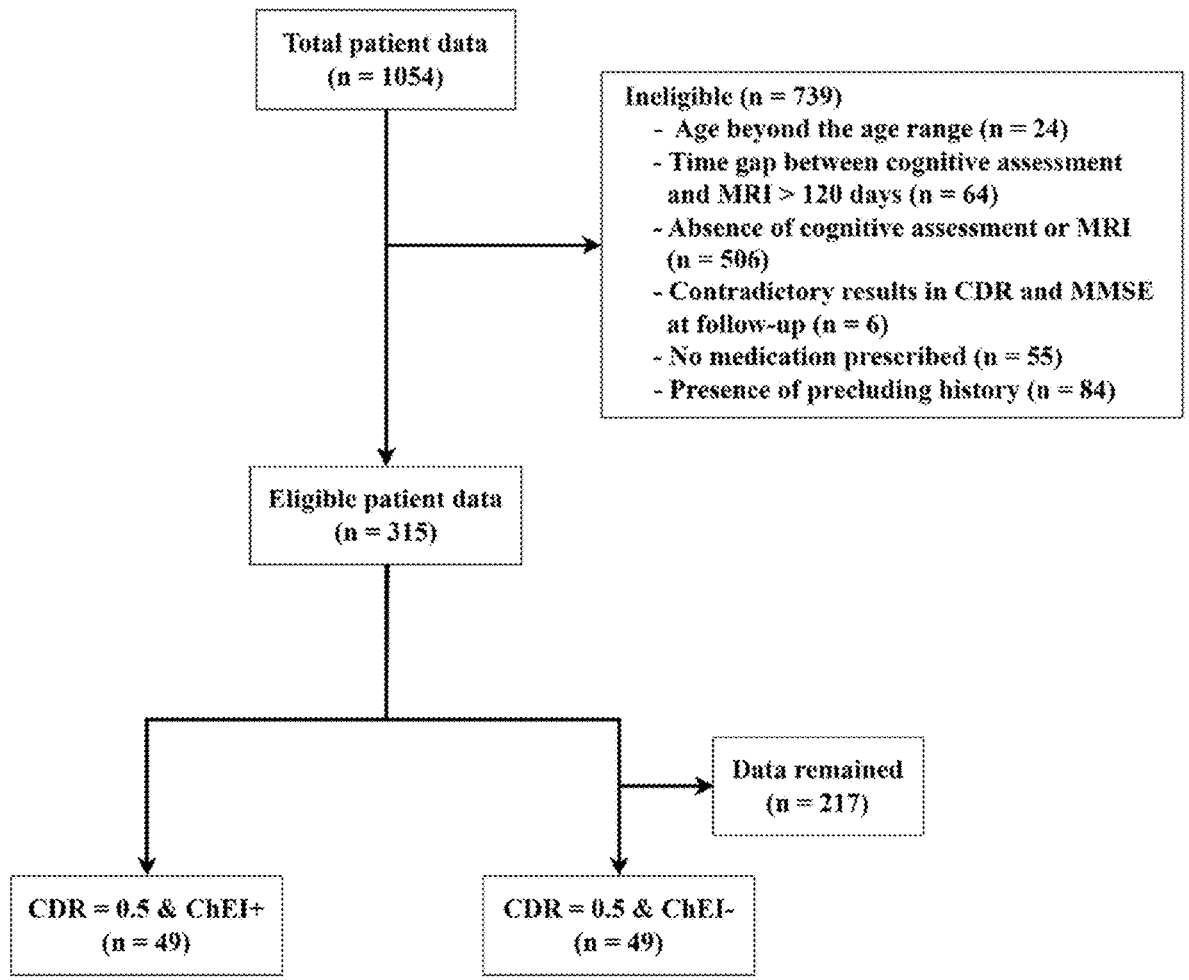
FIG. 27 shows a flow chart of data selection from the ChEI treatment database of Example 4.

Data Selection Results:

The flow chart of data selection in the Shuan Ho ChEI treatment database and the resulting sample size was shown in FIG. 27. In a total of 1054 patient data, 739 data were first excluded due to ineligible conditions as described in FIG. 27. In the 315 eligible patient data, data that met the criteria of either ChEI+ or ChEI− were selected. Among them, only 49 data belonged to MCI (i.e. CDR=0.5 at baseline) with ChEI+. To match the sample number of 49 in the ChEI+ group, 49 data of MCI with ChEI− were retrieved sequentially from the remaining data. Demographic data of the two groups were listed in Table 5. There was no significant difference between the two groups in each of the demographic items and imaging biomarkers.

TABLE 5

Demographics of the ChEI+ and ChEI− groups.

| | ChEI+ (n = 49) | ChEI− (n = 49) | p-Value |
|---|---|---|---|
| Age (year) | 74.97 ± 7.80 | 73.84 ± 8.56 | 0.359$^a$ |
| Gender (M/F) | 23(47%)/ 26 (53%) | 26(53%)/ 23(47%) | 0.758$^a$ |
| Treatment Duration (year) | 2.65 ± 0.74 | 2.49 ± 0.45 | 0.189$^a$ |
| MMSE at entry | 19.24 ± 4.01 | 19.76 ± 4.90 | 0.574$^a$ |
| Education (year) | 6.41 ± 4.41 | 7.24 ± 4.54 | 0.357$^a$ |
| MTA | 1.35 ± 1.01 | 1.54 ± 1.00 | 0.342$^a$ |

TABLE 5-continued

Demographics of the ChEI+ and ChEI- groups.

| | ChEI+ (n = 49) | ChEI- (n = 49) | p-Value |
|---|---|---|---|
| FAZEKAS | 1.69 ± 0.98 | 1.57 ± 0.96 | $0.534^a$ |
| Living Status (n) | | | $0.149^b$ |
| Solitary | 4 | 1 | |
| With Family | 45 | 46 | |
| Nursing Home | 0 | 2 | |
| Medicine Agent [n(Dose)] | | | $0.306^b$ (Agent) |
| Rivastigmine | 18 (7.64 mg/day) | 23 (7.08 mg/day) | $0.110^a$ (Dose) |
| Donepezil | 31 (8.55 mg/day) | 26 (9.42 mg/day) | $0.483^a$ (Dose) |
| Scanner (n) | | | $0.662^b$ |
| Discovery MR 750 | 23 | 19 | |
| Optima MR360 | 10 | 10 | |
| Signa HDxt | 16 | 20 | |

(p-value$^a$): Two-sample t-test;
(p-value$^b$): Chi-square test

Gray Matter Brain Age Model:

The present invention retrieved 72 T1 FLATR data from the Shuan Ho health check-up database (female=34, age: mean=63.0, S.D.=7.23, minimal=49.8, maximal=76.6, median=64.0 years) and 290 T1 MPRAGE data from OASJS-3 (female=171, age: mean=67.84, S.D.=7.63, minimal=49.6, maximal=84.7, median=68.5 years) were pooled to build a gray matter brain age model.

There was no age-related dependence between PAD and chronological age after bias correction (Pearson's correlation r=0.07, p=0.5589). The leave-one-out method showed MAE of 6.73 years for the constructed gray matter brain age model. There was significant association between brain age and chronological age (Pearson's correlation r=0.69, $p=2.026 \times 10^{-11}$).

Figure 28:
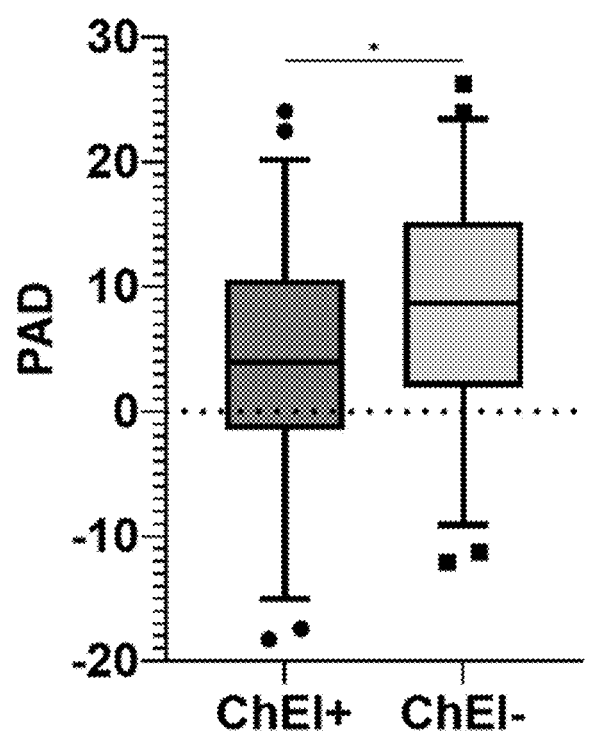
FIG. 28 shows a chart of comparison of PAD between the ChEI− and ChEI+ groups. Box plot was graphed according to 5-95 percentile; the dots above and below are the outliers of Example 4.

Comparison of PAD Between ChEI+ and ChEI- Groups:

Shapiro Wilk Test showed normal distributions of PAD in ChEI+(statistic=0.987, df=49, p=0.853) and ChEI- (statistic=0.988, df=49, p=0.907). Levene Test showed that variance equality of the two MCI groups could be assumed (statistic=0.36, p=0.851). The ChEI+ group showed a lower value of PAD (4.09±9.33 years) than the ChEI- group (8.19±9.06 years), as shown in FIG. 28. A two-sample t-test showed that the difference was statistically significant (p=0.030, Cohen's d=−0.441).

No significant association was found between PAD and Fazekas scale (Pearson's correlation r=0.0788, p=0.4403), while there was significant association between PAD and MTA score (Pearson's correlation r=0.2121, p=0.036).

Medial temporal atrophy (MTA) (Scheltens et al., 1995) is an approach for an examiner to visually scoring the brain atrophy condition based on three features: (1) width of the choroid fissure, (2) width of the temporal horn of the lateral ventricle, and (3) height of the hippocampus. MTA score ranges 0 to 4:

(1) Score 0: no CSF is visible around the hippocampus
(2) Score 1: choroid fissure is slightly widened
(3) Score 2: moderate widening of the choroid fissure, mild enlargement of the temporal horn and mild loss of hippocampal height
(4) Score 3: marked widening of the choroid fissure, moderate enlargement of the temporal horn, and moderate loss of hippocampal height
(5) Score 4: marked widening of the choroid fissure, marked enlargement of the temporal horn, and the hippocampus is markedly atrophied and internal structure is lost.

In one embodiment, the present invention predicts the therapeutic efficacy and efficiency of a treatment (e.g. ChEI) based on the PAD determined for a patient at the time when the patient start to receive the treatment. In the process of prediction, the present invention compares the PAD determined for the patient with a reference value. When the patient's PAD is greater than the reference value, the patient is predicted to have negative responses to the treatment, while a patient with PAD lower than the reference value is predicted to have positive responses.

In one embodiment, the reference value is determined by a predetermined brain age model using brain images of a group of patient demonstrating positive responses to the treatment, and brain images of a group of patient demonstrating negative responses to the treatment.

In one embodiment, according to the receiver operating characteristic (ROC) analysis, the area under curve (AUC) is 0.622. The reference value is 8.47 years, which achieves sensitivity 0.53 and specificity 0.69. Therefore, in one embodiment, the range of reference value is between 3 years and 14 years.

In one embodiment, the range of reference value is between 4 years and 13 years. In one embodiment, the range of reference value is between 5 years and 12 years. In one embodiment, the range of reference value is between 6 years and 11 years. In one embodiment, the range of reference value is between 7 years and 10 years. In one embodiment, the range of reference value is between 8 years and 9 years.

Discussion

Significance of the Study:

The present invention has shown that gray matter brain age can predict cognitive outcomes of patients with MCI under ChEI treatment. Patients with cognitive decline 2-3 years post treatment exhibited advanced baseline brain age (PAD=8.19±9.06 years) as compared with those without cognitive decline (PAD=4.09±9.33 years). Presently, the results imply that gray matter brain age could be used by clinicians as a reference of prognosis in the management of MCI patients. Another contribution of the present invention is that all imaging data directly come from routine clinical examinations. Gray matter brain age can be built readily from the real world data without additional imaging time, favoring its clinical feasibility.

Brain Age Predicts ChEI Response in MCI:

The present invention is the first study using brain age technology to predict ChEI response in patients with MCI. Previous studies used gray matter or white matter brain age at baseline to predict cognitive outcomes of MCI in 1 to 3 years. In those studies, ChEI treatment or other interventions were not prescribed, and so the prediction was made regarding the natural course of MCI. They found that conversion of MCI to AD was associated with increased brain age. The present invention further found that even with ChEI treatment, cognitive decline was also associated with increased brain age at baseline. The results imply that MCI patients with advanced brain age presents unfavorable gray matter conditions of the brain, which is susceptible to cognitive decline or AD conversion and is more difficult to be benefitted from ChEI treatment. This explanation is plausible because atrophic gray matter, as represented by advanced gray matter brain age, might mean depleted post-synaptic neurons of the cholinergic pathways. In this case, even though acetylcholine is elevated by means of ChEI, the effect is suboptimal due to the paucity of post-synaptic neurons (Pozzi et al., 2022).

Moreover, the present invention found that gray matter brain age was significantly associated with MTA score but not Fazekas scale. The results highlight the role of gray matter brain age; it is a proxy of hippocampal atrophy, not white matter degeneration induced by small vessel disease. These findings are consistent with the study by Cheng et al who recruited AD patients with CDR ranging from 0.5 to 2. They found that hippocampal atrophy but not white-matter changes predicts the long-term cognitive response to ChEI (Cheng et al., 2015).

Heterogeneous Studies of ChEI Response:

Multiple studies have investigated ChEI treatment outcomes, and the studies are heterogeneous, varying across the disease stage, different domains of outcomes and different follow-up time scales (Pozzi et al., 2022). The disease stage ranges from very mild dementia (MCI), mild, moderate to severe AD. The outcome domain includes cognitive domain as assessed by neuropsychological tests, MMSE, CDR or Alzheimer's Disease Assessment Scale-Cognitive (ADAS-cog), and functional domain as assessed by Instrumental Activities of Daily Living (IADL) or Physical Self-Maintenance Scale (PSMS). The time scales of follow up may vary from 6 months (short term) to 2 years or more (long term). The present study focused on long term cognitive outcomes in patients with MCI because this population is clinically relevant but most understudied.

Potential Covariates of ChEI Response:

The present invention found that PADs in ChEI+ and ChEI− were significantly different. Given that there are potential covariates of ChEI treatment response (Wattmo, 2013), the present invention compared the demographic variables of the two groups as listed in Table 5. It is found that there was no significant difference across all demographic variables. In addition, brain age results may be influenced by MRI scanners, and so the present invention further compared the data distribution of the three scanners. It is found that no significant difference between the two groups. Therefore, it is less likely that the significant difference in PAD was driven by the potential covariates or scanner types.

A Brain Age Model Across Different MRI Systems:

It is of note that a brain age model which has been trained by a dataset from a particular MRI machine cannot be directly applied to the data from another machine. If applied, there will be a large error in brain age prediction. To facilitate the generalization of the brain age model, a model transfer process should be taken (Jiang et al., 2019). The present invention used a co-train process to achieve model transfer (Chen et al., 2020). Because 72 normal data of Shuan Ho health check-up database are insufficient to build a brain age model, the present invention pooled them with 290 normal data in OASIS-3 to build the model. The resulting model constituted data from 6 different MRI systems, including two vendors and two different magnetic fields. The results showed that the model performed reasonably well (MAE=6.73 years) when it was to be applied to the patient data acquired from the same scanners as the 72 normal data. Furthermore, it is found that brain age derived from this model was able to distinguish the ChEI+ and ChEI− groups with statistical significance. The results indicate that if the training data come from different MRI machines, the trained model could be applied to these MRI systems simultaneously. This could potentially facilitate the process of model generalization.

Potential Application of Brain Age to Novel MCI Therapeutics:

Since 2021 FDA has approved several new drugs, e.g. Aducanumab and Lecanemab, for patients with MCI or prodromal AD, and there are a few more such as Donanemab and Solanezumab undergoing phase three clinical trials (Lee et al., 2022). These drugs belong to monoclonal antibody drugs targeting beta amyloid (Aβ) fibrils, and have shown a modest effect of slowing down the cognitive decline (~30%). However, a fraction of patients exhibited severe adverse reactions including brain edema and micro-bleeding. Since the present study has shown that capability of brain age to predict cognitive outcome in MCI under ChEI treatment, it can be used in clinical trials for novel therapeutics of MCI in patient stratification and prognostication.

CONCLUSION

The present invention discloses that the gray matter brain age model built from the real world MRI data serve as a potential biomarker to predict cognitive outcomes in patients with MCI 2 years after ChEI treatment. Thus, the present invention aids patient stratification and prognostication in the development of novel therapeutics in MCI.

The foregoing description of the exemplary embodiments of the invention has been presented only for the purposes of illustration and description and is not intended to be exhaustive or to limit the invention to the precise forms disclosed. Many modifications and variations are possible in light of the above teaching.

While there has been shown several and alternate embodiments of the present invention, it is to be understood that certain changes can be made as would be known to one skilled in the art without departing from the underlying scope of the invention as is discussed and set forth above and below including claims and drawings. Furthermore, the embodiments described above and claims set forth below are only intended to illustrate the principles of the present invention and are not intended to limit the scope of the invention to the disclosed elements.

References cited in the instant application, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in the description of this invention, are incorporated herein by reference in their entireties and to the same extent as if each reference was individually incorporated by reference.

What is claimed is:

1. A method of determining and predicting a brain atrophy condition for an individual using the individual's predicted age difference (PAD), the method comprising:
   (1) acquiring at least one brain image of the individual;
   (2) processing the brain image to obtain at least one feature of the brain image;
   (3) generating a PAD value of the individual based on the at least one feature of the image; and
   (4) determining a brain atrophy condition of the individual based on the PAD value.

2. The method of determining and predicting a brain atrophy condition for an individual using the individual's PAD according to claim 1, wherein:
   the at least one brain image is a brain MRI image.

3. The method of determining and predicting a brain atrophy condition for an individual using the individual's PAD according to claim 2, wherein:

the brain MRI image comprises an MRI image of a gray matter region of the individual's brain.

4. The method of determining and predicting a brain atrophy condition for an individual using the individual's PAD according to claim 1 further comprising:
   determining a medial temporal atrophy (MTA) score based on the PAD value.

5. The method of determining and predicting a brain atrophy condition for an individual using the individual's PAD according to claim 1, wherein:
   the PAD value of the individual is generated using a pre-established prediction model; and the pre-established prediction model comprises at least a brain age model.

6. The method of determining and predicting a brain atrophy condition for an individual using the individual's PAD according to claim 5, wherein:
   the step of processing of the medical brain image comprises at least one step of spatial normalization process.

7. The method of determining and predicting a brain atrophy condition for an individual using the individual's PAD according to claim 6, wherein:
   the step of processing of the medical image further comprises at least one step of feature quantification process.

8. The method of determining and predicting a brain atrophy condition for an individual using the individual's PAD according to claim 1 further comprising:
   predicting the brain atrophy condition's future change based on the PAD value.

9. A non-transitory computer readable medium storing a program causing a computer to execute a process for determining and predicting a brain atrophy condition for an individual using the individual's PAD, the process comprising:
   (1) acquiring at least one brain image of the individual;
   (2) processing the brain image to obtain at least one feature of the brain image;
   (3) generating a PAD value of the individual based on the at least one feature of the image; and
   (4) determining a brain atrophy condition of the individual based on the PAD value.

10. The non-transitory computer readable medium storing a program causing a computer to execute a process according to claim 9, wherein:
    the at least one brain image is a brain MRI image.

11. The non-transitory computer readable medium storing a program causing a computer to execute a process according to claim 10, wherein:
    the brain MRI image comprises an MRI image of a gray matter region of the individual's brain.

12. The non-transitory computer readable medium storing a program causing a computer to execute a process according to claim 9 further comprising:
    determining a medial temporal atrophy (MTA) score based on the PAD value.

13. The non-transitory computer readable medium storing a program causing a computer to execute a process according to claim 9, wherein:
    the PAD value of the individual is generated using a pre-established prediction model; and the pre-established prediction model comprises at least a brain age model.

14. The non-transitory computer readable medium storing a program causing a computer to execute a process according to claim 13, wherein:
    the step of processing of the medical brain image comprises at least one step of spatial normalization process.

15. The non-transitory computer readable medium storing a program causing a computer to execute a process according to claim 14, wherein:
    the step of processing of the medical image further comprises at least one step of feature quantification process.

16. The non-transitory computer readable medium storing a program causing a computer to execute a process according to claim 9 further comprising:
    predicting the brain atrophy condition's future change based on the PAD value.

* * * * *